United States Patent
Altarac et al.

(10) Patent No.: US 9,393,055 B2
(45) Date of Patent: Jul. 19, 2016

(54) SPACER INSERTION INSTRUMENT

(71) Applicants: Moti Altarac, Irvine, CA (US); Shawn Tebbe, Oceanside, CA (US); Daniel H. Kim, Houston, TX (US)

(72) Inventors: Moti Altarac, Irvine, CA (US); Shawn Tebbe, Oceanside, CA (US); Daniel H. Kim, Houston, TX (US)

(73) Assignee: VertiFlex, Inc., San Clemente, CA (US)

( * ) Notice: Subject to any disclaimer, the term of this patent is extended or adjusted under 35 U.S.C. 154(b) by 262 days.

(21) Appl. No.: 14/089,692

(22) Filed: Nov. 25, 2013

(65) Prior Publication Data

US 2014/0081332 A1    Mar. 20, 2014

Related U.S. Application Data

(63) Continuation of application No. 12/338,793, filed on Dec. 18, 2008, now Pat. No. 8,613,747, and a continuation-in-part of application No. 12/205,511, filed on Sep. 5, 2008, now Pat. No. 8,123,782, said (Continued)

(51) Int. Cl.
| | |
|---|---|
| *A61B 17/68* | (2006.01) |
| *A61B 17/70* | (2006.01) |
| *A61B 17/02* | (2006.01) |
| *A61B 17/00* | (2006.01) |
| *A61F 2/00* | (2006.01) |

(52) U.S. Cl.
CPC ............ *A61B 17/7074* (2013.01); *A61B 17/025* (2013.01); *A61B 17/7065* (2013.01); *A61B 17/7067* (2013.01); *A61B 17/7062* (2013.01); *A61B 2017/00004* (2013.01); *A61B 2017/0256* (2013.01); *A61F 2/0077* (2013.01)

(58) Field of Classification Search
CPC . A61F 2/46; A61F 2/4611; A61F 2002/4622; A61F 2002/4627; A61B 17/7062–17/707
See application file for complete search history.

(56) References Cited

U.S. PATENT DOCUMENTS

| | | |
|---|---|---|
| 2,248,054 A | 7/1941 | Becker |
| 2,677,369 A | 5/1954 | Knowles |

(Continued)

FOREIGN PATENT DOCUMENTS

| | | |
|---|---|---|
| CA | 268461 A | 2/1927 |
| DE | 69507480 | 9/1999 |

(Continued)

OTHER PUBLICATIONS

European Search Report Application No. EP05849654.8; Applicant: The Board of Trustees of the Leland Stanford Junior University; Date of Completion: Jun. 21, 2011, 4 pages.

(Continued)

*Primary Examiner* — Christopher D Prone
(74) *Attorney, Agent, or Firm* — Perkins Coie LLP

(57) ABSTRACT

A percutaneous and minimally invasive instrument for inserting an interspinous process spacer into a patient is disclosed. The insertion instrument includes a first assembly connected to a handle assembly. The first assembly includes an inner shaft located inside an outer shaft and configured for relative translational motion with respect to the outer shaft. The relative translational motion causes one of the outer or inner shafts to move with respect to the other and thereby deflect at least one prong formed on one of the inner or outer shafts wherein such deflection causes engagement with a juxtapositioned interspinous spacer. The instrument further includes a driving tool configured for removable insertion into a proximal end of a passageway of the instrument.

21 Claims, 21 Drawing Sheets

Related U.S. Application Data application No. 12/338,793 is a continuation-in-part of application No. 12/220,427, filed on Jul. 24, 2008, now Pat. No. 8,277,488, said application No. 12/338,793 is a continuation-in-part of application No. 12/217,662, filed on Jul. 8, 2008, now Pat. No. 8,273,108, said application No. 12/338,793 is a continuation-in-part of application No. 12/148,104, filed on Apr. 16, 2008, now Pat. No. 8,292,922, said application No. 12/338,793 is a continuation-in-part of application No. 11/593,995, filed on Nov. 7, 2006, now Pat. No. 8,425,559, and a continuation-in-part of application No. 11/582,874, filed on Oct. 18, 2006, now Pat. No. 8,128,662, and a continuation-in-part of application No. 11/314,712, filed on Dec. 20, 2005, now Pat. No. 8,152,837, and a continuation-in-part of application No. 11/190,496, filed on Jul. 26, 2005, now Pat. No. 8,409,282, and a continuation-in-part of application No. 11/079,006, filed on Mar. 10, 2005, now Pat. No. 8,012,207, and a continuation-in-part of application No. 11/052,002, filed on Feb. 4, 2005, now Pat. No. 8,317,864, and a continuation-in-part of application No. 11/006,502, filed on Dec. 6, 2004, now Pat. No. 8,123,807, and a continuation-in-part of application No. 10/970,843, filed on Oct. 20, 2004, now Pat. No. 8,167,944.

(60) Provisional application No. 61/008,418, filed on Dec. 19, 2007, provisional application No. 60/967,805, filed on Sep. 7, 2007, provisional application No. 60/961,741, filed on Jul. 24, 2007, provisional application No. 60/958,876, filed on Jul. 9, 2007, provisional application No. 60/923,971, filed on Apr. 17, 2007, provisional application No. 60/923,841, filed on Apr. 16, 2007.

(56) References Cited

U.S. PATENT DOCUMENTS

| | | |
|---|---|---|
| 3,242,120 A | 3/1966 | Steuber |
| 3,486,505 A | 12/1969 | Morrison |
| 3,648,691 A | 3/1972 | Lumb et al. |
| 3,986,383 A | 10/1976 | Petteys |
| 4,545,374 A | 10/1985 | Jacobson |
| 4,632,101 A | 12/1986 | Freedland |
| 4,685,447 A | 8/1987 | Iversen et al. |
| 4,799,484 A | 1/1989 | Smith et al. |
| 4,863,476 A | 9/1989 | Shepperd |
| 4,895,564 A | 1/1990 | Farrell |
| 4,986,831 A | 1/1991 | King et al. |
| 5,011,484 A | 4/1991 | Breard et al. |
| 5,015,247 A | 5/1991 | Michelson |
| 5,019,081 A | 5/1991 | Watanabe |
| 5,059,193 A | 10/1991 | Kuslich |
| 5,092,866 A | 3/1992 | Breard et al. |
| 5,178,628 A | 1/1993 | Otsuka et al. |
| 5,180,393 A | 1/1993 | Commarmond et al. |
| 5,182,281 A | 1/1993 | Frigola-Constansa et al. |
| 5,188,281 A | 2/1993 | Fujiwara et al. |
| 5,192,281 A | 3/1993 | de la Caffiniere |
| 5,195,526 A | 3/1993 | Michelson |
| 5,298,253 A | 3/1994 | LeFiles et al. |
| 5,368,594 A | 11/1994 | Martin et al. |
| 5,390,683 A | 2/1995 | Pisharodi |
| 5,415,661 A | 5/1995 | Holmes |
| 5,456,722 A | 10/1995 | McLeod et al. |
| 5,462,738 A | 10/1995 | LeFiles et al. |
| 5,472,452 A | 12/1995 | Trott |
| 5,484,437 A | 1/1996 | Michelson |
| 5,487,739 A | 1/1996 | Aebischer et al. |
| 5,489,308 A | 2/1996 | Kuslich et al. |
| 5,496,318 A | 3/1996 | Howland et al. |
| 5,531,748 A | 7/1996 | de la Caffiniere et al. |
| 5,549,679 A | 8/1996 | Kuslich |
| 5,571,189 A | 11/1996 | Kuslich |
| 5,591,165 A | 1/1997 | Jackson |
| 5,609,634 A | 3/1997 | Voydeville et al. |
| 5,609,636 A | 3/1997 | Kohrs et al. |
| 5,645,599 A | 7/1997 | Samani et al. |
| 5,654,599 A | 8/1997 | Casper |
| 5,658,337 A | 8/1997 | Kohrs et al. |
| 5,674,295 A | 10/1997 | Ray et al. |
| 5,700,264 A | 12/1997 | Zucherman et al. |
| 5,725,582 A | 3/1998 | Bevan et al. |
| 5,741,253 A | 4/1998 | Michelson |
| 5,746,720 A | 5/1998 | Stouder, Jr. |
| 5,762,629 A | 6/1998 | Kambin |
| 5,836,948 A | 11/1998 | Zucherman et al. |
| 5,860,977 A | 1/1999 | Zucherman et al. |
| 5,863,948 A | 1/1999 | Epstein et al. |
| 5,876,404 A | 3/1999 | Zucherman et al. |
| RE36,211 E | 5/1999 | Nonomura et al. |
| 5,904,636 A | 5/1999 | Chen et al. |
| 5,904,686 A | 5/1999 | Zucherman et al. |
| 5,928,207 A | 7/1999 | Pisano et al. |
| 5,948,017 A | 9/1999 | Taheri |
| 5,972,015 A | 10/1999 | Scribner et al. |
| 6,039,761 A | 3/2000 | Li et al. |
| 6,045,552 A | 4/2000 | Zucherman et al. |
| 6,048,342 A | 4/2000 | Zucherman et al. |
| 6,048,345 A | 4/2000 | Berke et al. |
| 6,066,154 A | 5/2000 | Reiley et al. |
| 6,068,630 A | 5/2000 | Zucherman et al. |
| 6,074,390 A | 6/2000 | Zucherman et al. |
| 6,080,155 A | 6/2000 | Michelson |
| 6,080,157 A | 6/2000 | Cathro et al. |
| 6,090,112 A | 7/2000 | Zucherman et al. |
| 6,096,038 A | 8/2000 | Michelson |
| 6,102,928 A | 8/2000 | Bonutti |
| D433,193 S | 10/2000 | Gaw et al. |
| 6,132,464 A | 10/2000 | Martin et al. |
| 6,149,642 A | 11/2000 | Gerhart et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,215 A | 12/2000 | Urbahns et al. |
| 6,179,873 B1 | 1/2001 | Zientek |
| 6,183,471 B1 | 2/2001 | Zucherman et al. |
| 6,190,387 B1 | 2/2001 | Zucherman et al. |
| 6,225,048 B1 | 5/2001 | Soderberg-Naucler et al. |
| 6,235,030 B1 | 5/2001 | Zucherman et al. |
| 6,238,397 B1 | 5/2001 | Zucherman et al. |
| 6,264,651 B1 | 7/2001 | Underwood et al. |
| 6,264,656 B1 | 7/2001 | Michelson |
| 6,267,765 B1 | 7/2001 | Taylor et al. |
| 6,270,498 B1 | 8/2001 | Michelson |
| 6,280,444 B1 | 8/2001 | Zucherman et al. |
| 6,312,431 B1 | 11/2001 | Asfora |
| 6,332,882 B1 | 12/2001 | Zucherman et al. |
| 6,332,883 B1 | 12/2001 | Zucherman et al. |
| 6,336,930 B1 | 1/2002 | Stalcup et al. |
| 6,348,053 B1 | 2/2002 | Cachia |
| 6,364,883 B1 | 4/2002 | Santilli |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,387,130 B1 | 5/2002 | Stone et al. |
| 6,395,032 B1 | 5/2002 | Gauchet |
| 6,402,740 B1 | 6/2002 | Ellis et al. |
| 6,402,750 B1 | 6/2002 | Atkinson et al. |
| 6,402,784 B1 | 6/2002 | Wardlaw et al. |
| 6,413,228 B1 | 7/2002 | Hung et al. |
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,443,988 B2 | 9/2002 | Felt et al. |
| 6,447,547 B1 | 9/2002 | Michelson |
| 6,451,019 B1 | 9/2002 | Zucherman et al. |
| 6,451,020 B1 | 9/2002 | Zucherman et al. |

(56) References Cited

U.S. PATENT DOCUMENTS

| | | |
|---|---|---|
| 6,471,976 B1 | 10/2002 | Taylor et al. |
| 6,478,796 B2 | 11/2002 | Zucherman et al. |
| 6,478,822 B1 | 11/2002 | Leroux et al. |
| 6,500,178 B2 | 12/2002 | Zucherman et al. |
| 6,514,256 B2 | 2/2003 | Zucherman et al. |
| 6,530,925 B2 | 3/2003 | Boudard et al. |
| 6,558,333 B2 | 5/2003 | Gilboa et al. |
| 6,565,570 B2 | 5/2003 | Sterett et al. |
| 6,572,617 B1 | 6/2003 | Senegas et al. |
| 6,575,981 B1 | 6/2003 | Boyd et al. |
| 6,579,281 B2 | 6/2003 | Palmer et al. |
| 6,579,319 B2 | 6/2003 | Goble et al. |
| 6,582,433 B2 | 6/2003 | Yun |
| 6,582,451 B1 | 6/2003 | Marucci et al. |
| 6,599,292 B1 | 7/2003 | Ray |
| 6,610,065 B1 | 8/2003 | Branch et al. |
| 6,610,091 B1 | 8/2003 | Reiley |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,663,637 B2 | 12/2003 | Dixon et al. |
| 6,679,886 B2 | 1/2004 | Weikel et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,702,847 B2 | 3/2004 | DiCarlo |
| 6,712,819 B2 | 3/2004 | Zucherman et al. |
| 6,716,245 B2 | 4/2004 | Pasquet et al. |
| 6,733,534 B2 | 5/2004 | Sherman |
| 6,746,485 B1 | 6/2004 | Zucherman et al. |
| 6,761,720 B1 | 7/2004 | Senegas et al. |
| 6,783,529 B2 | 8/2004 | Hover et al. |
| 6,783,546 B2 | 8/2004 | Zucherman et al. |
| 6,796,983 B1 | 9/2004 | Zucherman et al. |
| 6,805,697 B1 | 10/2004 | Helm et al. |
| 6,835,205 B2 | 12/2004 | Atkinson et al. |
| 6,840,944 B2 | 1/2005 | Suddaby |
| 6,858,029 B2 | 2/2005 | Yeh |
| 6,869,398 B2 | 3/2005 | Obenchain et al. |
| 6,875,212 B2 | 4/2005 | Shaolian et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Arnin et al. |
| 6,974,478 B2 | 12/2005 | Reiley et al. |
| 7,011,685 B2 | 3/2006 | Arnin et al. |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,179,225 B2 | 2/2007 | Shluzas et al. |
| 7,187,064 B2 | 3/2007 | Tzu et al. |
| 7,189,234 B2 | 3/2007 | Zucherman et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |
| 7,223,289 B2 | 5/2007 | Trieu et al. |
| 7,229,441 B2 | 6/2007 | Trieu et al. |
| 7,238,204 B2 | 7/2007 | Le Couedic et al. |
| 7,252,673 B2 | 8/2007 | Lim |
| 7,273,496 B2 | 9/2007 | Mitchell |
| 7,282,063 B2 | 10/2007 | Cohen et al. |
| 7,297,162 B2 | 11/2007 | Mujwid |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,390,330 B2 | 6/2008 | Harp |
| 7,410,501 B2 | 8/2008 | Michelson |
| 7,442,208 B2 | 10/2008 | Mathieu et al. |
| 7,445,637 B2 | 11/2008 | Taylor |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,510,567 B2 | 3/2009 | Zucherman et al. |
| 7,520,887 B2 | 4/2009 | Maxy et al. |
| 7,520,899 B2 | 4/2009 | Zucherman et al. |
| 7,547,308 B2 | 6/2009 | Bertagnoli et al. |
| 7,549,999 B2 | 6/2009 | Zucherman et al. |
| 7,550,009 B2 | 6/2009 | Arnin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,585,313 B2 | 9/2009 | Kwak et al. |
| 7,585,316 B2 | 9/2009 | Trieu |
| 7,591,851 B2 | 9/2009 | Winslow et al. |
| 7,601,170 B2 | 10/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,950 B2 | 12/2009 | Baccelli et al. |
| 7,658,752 B2 | 2/2010 | Labrom et al. |
| 7,662,187 B2 | 2/2010 | Zucherman et al. |
| 7,666,186 B2 | 2/2010 | Harp |
| 7,666,209 B2 | 2/2010 | Zucherman et al. |
| 7,666,228 B2 | 2/2010 | Le Couedic et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,695,513 B2 | 4/2010 | Zucherman et al. |
| 7,699,852 B2 | 4/2010 | Frankel et al. |
| 7,699,873 B2 | 4/2010 | Stevenson et al. |
| 7,727,233 B2 | 6/2010 | Blackwell et al. |
| 7,727,241 B2 | 6/2010 | Gorensek et al. |
| 7,731,751 B2 | 6/2010 | Butler et al. |
| 7,742,795 B2 | 6/2010 | Stone et al. |
| 7,749,231 B2 | 7/2010 | Bonvallet et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,758,647 B2 | 7/2010 | Arnin et al. |
| 7,763,028 B2 | 7/2010 | Lim et al. |
| 7,763,050 B2 | 7/2010 | Winslow et al. |
| 7,763,051 B2 | 7/2010 | Labrom et al. |
| 7,763,073 B2 | 7/2010 | Hawkins et al. |
| 7,763,074 B2 | 7/2010 | Altarac et al. |
| 7,766,967 B2 | 8/2010 | Francis |
| 7,776,090 B2 | 8/2010 | Winslow et al. |
| 7,780,709 B2 | 8/2010 | Bruneau et al. |
| 7,789,898 B2 | 9/2010 | Peterman |
| 7,794,476 B2 | 9/2010 | Wisnewski |
| 7,803,190 B2 | 9/2010 | Zucherman et al. |
| 7,806,911 B2 | 10/2010 | Peckham |
| 7,811,308 B2 | 10/2010 | Arnin et al. |
| 7,811,322 B2 | 10/2010 | Arnin et al. |
| 7,811,323 B2 | 10/2010 | Arnin et al. |
| 7,811,324 B2 | 10/2010 | Arnin et al. |
| 7,811,330 B2 | 10/2010 | Arnin et al. |
| 7,819,921 B2 | 10/2010 | Grotz |
| 7,828,822 B2 | 11/2010 | Zucherman et al. |
| 7,828,849 B2 | 11/2010 | Lim |
| 7,833,272 B2 | 11/2010 | Arnin et al. |
| 7,837,687 B2 | 11/2010 | Harp |
| 7,837,688 B2 | 11/2010 | Boyer, II et al. |
| 7,837,700 B2 | 11/2010 | Harp |
| 7,837,734 B2 | 11/2010 | Zucherman et al. |
| 7,846,183 B2 | 12/2010 | Blain |

(56) References Cited

U.S. PATENT DOCUMENTS

| | | |
|---|---|---|
| 7,846,185 B2 | 12/2010 | Carls et al. |
| 7,846,186 B2 | 12/2010 | Taylor |
| 7,857,815 B2 | 12/2010 | Zucherman et al. |
| 7,862,569 B2 | 1/2011 | Zucherman et al. |
| 7,862,586 B2 | 1/2011 | Malek |
| 7,862,590 B2 | 1/2011 | Lim et al. |
| 7,862,592 B2 | 1/2011 | Peterson et al. |
| 7,862,615 B2 | 1/2011 | Carli et al. |
| 7,867,276 B2 | 1/2011 | Matge et al. |
| 7,871,426 B2 | 1/2011 | Chin et al. |
| 7,896,879 B2 | 3/2011 | Solsberg et al. |
| 7,942,830 B2 | 5/2011 | Solsberg et al. |
| 7,955,392 B2 | 6/2011 | Dewey et al. |
| 8,012,207 B2 | 9/2011 | Kim |
| 8,025,684 B2 | 9/2011 | Garcia-Bengochea et al. |
| 8,057,513 B2 | 11/2011 | Kohm et al. |
| 8,062,332 B2 | 11/2011 | Cunningham et al. |
| 8,100,823 B2 | 1/2012 | Harp |
| 8,123,782 B2 | 2/2012 | Altarac et al. |
| 8,123,807 B2 | 2/2012 | Kim |
| 8,128,662 B2 | 3/2012 | Altarac et al. |
| 8,152,837 B2 | 4/2012 | Altarac et al. |
| 8,167,944 B2 | 5/2012 | Kim |
| 8,226,690 B2 | 7/2012 | Altarac et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,317,864 B2 | 11/2012 | Kim |
| 8,409,282 B2 | 4/2013 | Kim |
| 8,425,559 B2 | 4/2013 | Tebbe et al. |
| 8,608,762 B2 | 12/2013 | Solsberg et al. |
| 8,613,747 B2 | 12/2013 | Altarac et al. |
| 8,628,574 B2 | 1/2014 | Altarac et al. |
| 8,696,671 B2 | 4/2014 | Solsberg et al. |
| 8,734,477 B2 | 5/2014 | Solsberg et al. |
| 8,740,948 B2 | 6/2014 | Reglos et al. |
| 8,845,726 B2 | 9/2014 | Tebbe et al. |
| 8,864,828 B2 | 10/2014 | Altarac et al. |
| 8,882,772 B2 | 11/2014 | Solsberg et al. |
| 8,894,653 B2 | 11/2014 | Solsberg et al. |
| 8,900,271 B2 | 12/2014 | Kim |
| 8,945,183 B2 | 2/2015 | Altarac et al. |
| 9,023,084 B2 | 5/2015 | Kim |
| 9,039,742 B2 | 5/2015 | Altarac et al. |
| 9,119,680 B2 | 9/2015 | Altarac et al. |
| 9,125,692 B2 | 9/2015 | Kim |
| 9,155,570 B2 | 10/2015 | Altarac et al. |
| 9,155,572 B2 | 10/2015 | Altarac et al. |
| 9,161,783 B2 | 10/2015 | Altarac et al. |
| 9,186,186 B2 | 11/2015 | Reglos et al. |
| 9,211,146 B2 | 12/2015 | Kim |
| 2001/0031965 A1 | 10/2001 | Zucherman et al. |
| 2002/0042607 A1 | 4/2002 | Palmer et al. |
| 2002/0143331 A1 | 10/2002 | Zucherman et al. |
| 2003/0040746 A1 | 2/2003 | Mitchell et al. |
| 2003/0074075 A1 | 4/2003 | Thomas et al. |
| 2003/0149438 A1 | 8/2003 | Nichols et al. |
| 2003/0153976 A1 | 8/2003 | Cauthen et al. |
| 2003/0176921 A1 | 9/2003 | Lawson |
| 2003/0220650 A1 | 11/2003 | Major et al. |
| 2003/0233098 A1 | 12/2003 | Markworth |
| 2004/0087947 A1 | 5/2004 | Lim et al. |
| 2004/0167625 A1 | 8/2004 | Beyar et al. |
| 2004/0220568 A1 | 11/2004 | Zucherman et al. |
| 2005/0049708 A1 | 3/2005 | Atkinson et al. |
| 2005/0075634 A1 | 4/2005 | Zucherman et al. |
| 2005/0101955 A1 | 5/2005 | Zucherman et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0192586 A1 | 9/2005 | Zucherman et al. |
| 2005/0192671 A1 | 9/2005 | Bao et al. |
| 2005/0209603 A1 | 9/2005 | Zucherman et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0245937 A1 | 11/2005 | Winslow |
| 2005/0261768 A1 | 11/2005 | Trieu |
| 2005/0278036 A1 | 12/2005 | Leonard et al. |
| 2006/0036258 A1 | 2/2006 | Zucherman et al. |
| 2006/0064166 A1 | 3/2006 | Zucherman et al. |
| 2006/0074431 A1 | 4/2006 | Sutton et al. |
| 2006/0084976 A1 | 4/2006 | Borgstrom et al. |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0102269 A1 | 5/2006 | Uchida et al. |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0195102 A1 | 8/2006 | Malandain |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0241597 A1 | 10/2006 | Mitchell et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271044 A1 | 11/2006 | Petrini et al. |
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1 | 11/2006 | Zucherman et al. |
| 2006/0276801 A1 | 12/2006 | Yerby et al. |
| 2006/0276897 A1 | 12/2006 | Winslow et al. |
| 2006/0282077 A1 | 12/2006 | Labrom et al. |
| 2006/0282078 A1 | 12/2006 | Labrom et al. |
| 2007/0016196 A1 | 1/2007 | Winslow et al. |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0100340 A1 | 5/2007 | Lange et al. |
| 2007/0123863 A1 | 5/2007 | Winslow et al. |
| 2007/0123904 A1 | 5/2007 | Stad et al. |
| 2007/0161991 A1 | 7/2007 | Altarac et al. |
| 2007/0161993 A1 | 7/2007 | Lowery et al. |
| 2007/0173818 A1 | 7/2007 | Hestad et al. |
| 2007/0173821 A1 | 7/2007 | Trieu |
| 2007/0173822 A1 | 7/2007 | Bruneau et al. |
| 2007/0173823 A1 | 7/2007 | Dewey et al. |
| 2007/0173832 A1 | 7/2007 | Tebbe et al. |
| 2007/0173939 A1 | 7/2007 | Kim et al. |
| 2007/0179500 A1 | 8/2007 | Chin et al. |
| 2007/0185490 A1 | 8/2007 | Implicito |
| 2007/0191948 A1 | 8/2007 | Arnin et al. |
| 2007/0198045 A1 | 8/2007 | Morton et al. |
| 2007/0198091 A1 | 8/2007 | Boyer et al. |
| 2007/0203493 A1 | 8/2007 | Zucherman et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208345 A1 | 9/2007 | Marnay et al. |
| 2007/0208346 A1 | 9/2007 | Marnay et al. |
| 2007/0208366 A1 | 9/2007 | Pellegrino et al. |
| 2007/0210018 A1 | 9/2007 | Wallwiener et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0225814 A1 | 9/2007 | Atkinson et al. |
| 2007/0233068 A1 | 10/2007 | Bruneau et al. |

(56) References Cited

U.S. PATENT DOCUMENTS

| | | |
|---|---|---|
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0265626 A1 | 11/2007 | Seme |
| 2007/0270822 A1 | 11/2007 | Heinz |
| 2007/0270823 A1 | 11/2007 | Trieu et al. |
| 2007/0270824 A1 | 11/2007 | Lim et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2008/0015700 A1 | 1/2008 | Zucherman et al. |
| 2008/0021468 A1 | 1/2008 | Zucherman et al. |
| 2008/0021560 A1 | 1/2008 | Zucherman et al. |
| 2008/0021561 A1 | 1/2008 | Zucherman et al. |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071378 A1 | 3/2008 | Zucherman et al. |
| 2008/0086212 A1 | 4/2008 | Zucherman et al. |
| 2008/0108990 A1 | 5/2008 | Mitchell et al. |
| 2008/0114455 A1 | 5/2008 | Lange et al. |
| 2008/0132952 A1 | 6/2008 | Malandain et al. |
| 2008/0167655 A1 | 7/2008 | Wang et al. |
| 2008/0167656 A1 | 7/2008 | Zucherman et al. |
| 2008/0172057 A1 | 7/2008 | Zucherman et al. |
| 2008/0177272 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0183210 A1 | 7/2008 | Zucherman et al. |
| 2008/0188895 A1 | 8/2008 | Cragg et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234708 A1 | 9/2008 | Houser et al. |
| 2008/0234824 A1 | 9/2008 | Youssef et al. |
| 2008/0288075 A1 | 11/2008 | Zucherman et al. |
| 2008/0319550 A1 | 12/2008 | Altarac et al. |
| 2009/0012528 A1 | 1/2009 | Aschmann et al. |
| 2009/0118833 A1 | 5/2009 | Hudgins et al. |
| 2009/0125030 A1 | 5/2009 | Tebbe et al. |
| 2009/0138046 A1 | 5/2009 | Altarac et al. |
| 2009/0138055 A1 | 5/2009 | Altarac et al. |
| 2009/0222043 A1 | 9/2009 | Altarac et al. |
| 2009/0248079 A1 | 10/2009 | Kwak et al. |
| 2009/0292315 A1 | 11/2009 | Trieu |
| 2010/0042217 A1 | 2/2010 | Zucherman et al. |
| 2010/0082108 A1 | 4/2010 | Zucherman et al. |
| 2010/0131009 A1 | 5/2010 | Roebling et al. |
| 2010/0228092 A1 | 9/2010 | Ortiz et al. |
| 2010/0234889 A1 | 9/2010 | Hess |
| 2010/0262243 A1 | 10/2010 | Zucherman et al. |
| 2010/0280551 A1 | 11/2010 | Pool et al. |
| 2010/0305611 A1 | 12/2010 | Zucherman et al. |
| 2011/0245833 A1 | 10/2011 | Anderson |
| 2011/0313457 A1 | 12/2011 | Reglos et al. |
| 2012/0158063 A1 | 6/2012 | Altarac et al. |
| 2012/0226315 A1 | 9/2012 | Altarac et al. |
| 2012/0232552 A1 | 9/2012 | Morgenstern Lopez et al. |
| 2012/0303039 A1 | 11/2012 | Chin et al. |
| 2013/0012998 A1 | 1/2013 | Altarac et al. |
| 2013/0150886 A1 | 6/2013 | Altarac et al. |
| 2013/0165974 A1 | 6/2013 | Kim |
| 2013/0165975 A1 | 6/2013 | Tebbe et al. |
| 2013/0172932 A1 | 7/2013 | Altarac et al. |
| 2013/0172933 A1 | 7/2013 | Altarac et al. |
| 2013/0289399 A1 | 10/2013 | Choi et al. |
| 2013/0289622 A1 | 10/2013 | Kim |
| 2014/0214082 A1 | 7/2014 | Reglos et al. |
| 2014/0228884 A1 | 8/2014 | Altarac et al. |
| 2014/0275992 A1 | 9/2014 | Choi et al. |
| 2015/0150598 A1 | 6/2015 | Tebbe et al. |
| 2015/0150604 A1 | 6/2015 | Kim |
| 2015/0164560 A1 | 6/2015 | Altarac et al. |
| 2015/0374415 A1 | 12/2015 | Kim |

FOREIGN PATENT DOCUMENTS

| | | |
|---|---|---|
| EP | 322334 | 6/1989 |
| EP | 0767636 | 4/1997 |
| EP | 0768843 B1 | 4/1997 |
| EP | 0959792 B1 | 12/1999 |
| EP | 1027004 A1 | 8/2000 |
| EP | 1030615 A1 | 8/2000 |
| EP | 1138268 | 10/2001 |
| EP | 1330987 A1 | 7/2003 |
| EP | 1056408 B1 | 12/2003 |
| EP | 1343424 B1 | 9/2004 |
| EP | 1454589 A1 | 9/2004 |
| EP | 1148850 B1 | 4/2005 |
| EP | 1570793 A2 | 9/2005 |
| EP | 1299042 B1 | 3/2006 |
| EP | 1578314 B1 | 5/2007 |
| EP | 1675535 B1 | 5/2007 |
| EP | 1861046 A2 | 12/2007 |
| FR | 2681525 A1 | 3/1993 |
| FR | 2722980 A1 | 2/1996 |
| FR | 2816197 A1 | 5/2002 |

(56) References Cited

FOREIGN PATENT DOCUMENTS

| | | |
|---|---|---|
| FR | 2884136 A1 | 10/2006 |
| FR | 2888744 A1 | 1/2007 |
| SU | 988281 A1 | 1/1983 |
| WO | WO-9404088 A1 | 3/1994 |
| WO | WO-9426192 A1 | 11/1994 |
| WO | WO-9525485 A1 | 9/1995 |
| WO | WO-9531158 A1 | 11/1995 |
| WO | WO-9600049 A1 | 1/1996 |
| WO | WO-9829047 A1 | 7/1998 |
| WO | WO-9921500 A1 | 5/1999 |
| WO | WO-9921501 A1 | 5/1999 |
| WO | WO-9942051 A1 | 8/1999 |
| WO | WO-0013619 A1 | 3/2000 |
| WO | WO-0044319 A1 | 8/2000 |
| WO | WO-0044321 A2 | 8/2000 |
| WO | WO-0128442 A1 | 4/2001 |
| WO | WO-0191657 A1 | 12/2001 |
| WO | WO-0191658 A1 | 12/2001 |
| WO | WO-0203882 A2 | 1/2002 |
| WO | WO-0207623 A1 | 1/2002 |
| WO | WO-0207624 A1 | 1/2002 |
| WO | WO-02051326 A1 | 7/2002 |
| WO | WO-02067793 A2 | 9/2002 |
| WO | WO-02071960 A1 | 9/2002 |
| WO | WO-02076336 A2 | 10/2002 |
| WO | WO-03007791 A2 | 1/2003 |
| WO | WO-03007829 A1 | 1/2003 |
| WO | WO-03008016 A2 | 1/2003 |
| WO | WO-03015646 A2 | 2/2003 |
| WO | WO-03024298 A2 | 3/2003 |
| WO | WO-03045262 A2 | 6/2003 |
| WO | WO-03099147 A1 | 12/2003 |
| WO | WO-03101350 A1 | 12/2003 |
| WO | WO-2004073533 A1 | 9/2004 |
| WO | WO-2004110300 A2 | 12/2004 |
| WO | WO-2005009300 A1 | 2/2005 |
| WO | WO-2005013839 A2 | 2/2005 |
| WO | WO-2005025461 A2 | 3/2005 |
| WO | WO-2005041799 A1 | 5/2005 |
| WO | WO-2005044152 A1 | 5/2005 |
| WO | WO-2005055868 A2 | 6/2005 |
| WO | WO-2005079672 A2 | 9/2005 |
| WO | WO-2005086776 A2 | 9/2005 |
| WO | WO-2005115261 A1 | 12/2005 |
| WO | WO-2006033659 A2 | 3/2006 |
| WO | WO-2006034423 A2 | 3/2006 |
| WO | WO-2006039243 | 4/2006 |
| WO | WO-2006039260 A2 | 4/2006 |
| WO | WO-2006045094 A2 | 4/2006 |
| WO | WO-2006063047 A2 | 6/2006 |
| WO | WO-2006064356 A1 | 6/2006 |
| WO | WO-2006065774 A1 | 6/2006 |
| WO | WO-2006089085 A2 | 8/2006 |
| WO | WO-2006102269 A2 | 9/2006 |
| WO | WO-2006102428 A2 | 9/2006 |
| WO | WO-2006102485 A2 | 9/2006 |
| WO | WO-2006107539 A1 | 10/2006 |
| WO | WO-2006110462 A2 | 10/2006 |
| WO | WO-2006110464 A1 | 10/2006 |
| WO | WO-2006110767 A1 | 10/2006 |
| WO | WO-2006113080 A2 | 10/2006 |
| WO | WO-2006113406 A2 | 10/2006 |
| WO | WO-2006113814 A2 | 10/2006 |
| WO | WO-2006118945 A1 | 11/2006 |
| WO | WO-2006119235 A1 | 11/2006 |
| WO | WO-2006119236 A2 | 11/2006 |
| WO | WO-2006135511 A1 | 12/2006 |
| WO | WO-2007015028 A1 | 2/2007 |
| WO | WO-2007035120 A1 | 3/2007 |
| WO | WO-2007075375 A2 | 7/2007 |
| WO | WO-2007075788 A2 | 7/2007 |
| WO | WO-2007075791 A2 | 7/2007 |
| WO | WO-2007089605 A2 | 8/2007 |
| WO | WO-2007089905 A2 | 8/2007 |
| WO | WO-2007089975 A1 | 8/2007 |
| WO | WO-2007097735 A2 | 8/2007 |
| WO | WO-2007109402 A2 | 9/2007 |
| WO | WO-2007110604 A1 | 10/2007 |
| WO | WO-2007111795 A1 | 10/2007 |
| WO | WO-2007111979 A2 | 10/2007 |
| WO | WO-2007111999 A2 | 10/2007 |
| WO | WO-2007117882 A1 | 10/2007 |
| WO | WO-2007121070 A2 | 10/2007 |
| WO | WO-2007127550 A2 | 11/2007 |
| WO | WO-2007127588 A1 | 11/2007 |
| WO | WO-2007127677 A1 | 11/2007 |
| WO | WO-2007127689 A2 | 11/2007 |
| WO | WO-2007127694 A2 | 11/2007 |
| WO | WO-2007127734 A2 | 11/2007 |
| WO | WO-2007127736 A2 | 11/2007 |
| WO | WO-2007131165 A2 | 11/2007 |
| WO | WO-2007134113 A2 | 11/2007 |
| WO | WO-2008009049 A1 | 1/2008 |
| WO | WO-2008048645 A2 | 4/2008 |
| WO | WO-2008057506 A2 | 5/2008 |
| WO | WO-2008130564 A1 | 10/2008 |
| WO | WO-2009014728 A2 | 1/2009 |
| WO | WO-2009033093 A1 | 3/2009 |
| WO | WO-2009086010 A2 | 7/2009 |
| WO | WO-2009091922 A2 | 7/2009 |
| WO | WO-2009094463 A2 | 7/2009 |
| WO | WO-2009114479 A2 | 9/2009 |
| WO | WO-2011084477 A2 | 7/2011 |
| WO | WO-2015171814 A1 | 11/2015 |

OTHER PUBLICATIONS

International Search Report and Written Opinion; Application No. PCT/US2005/038026; Mailing Date: Apr. 22, 2008, 9 pages.
International Search Report and Written Opinion; Application No. PCT/US2005/044256; Mailing Date: Jul. 28, 2006, 7 pages.
International Search Report and Written Opinion; Application No. PCT/US2006/047824; Mailing Date: Oct. 16, 2008, 17 pages.
International Search Report and Written Opinion; Application No. PCT/US2006/048611; Mailing Date: Oct. 14, 2008; 10 pages.
International Search Report and Written Opinion; Application No. PCT/US2006/048614; Mailing Date: Feb. 3, 2006; 23 pages.
International Search Report and Written Opinion; Application No. PCT/US2007/022171; Mailing Date: Apr. 15, 2008, 9 pages.
International Search Report and Written Opinion; Application No. PCT/US2007/023312; Mailing Date: May 22, 2008, 14 pages.
International Search Report and Written Opinion; Application No. PCT/US2008/004901; Mailing Date: Aug. 19, 2008, 7 pages.
International Search Report and Written Opinion; Application No. PCT/US2008/008382; Mailing Date: Mar. 2, 2009, 13 pages.
International Search Report and Written Opinion; Application No. PCT/US2008/008983; Mailing Date: Feb. 23, 2009, 7 pages.
International Search Report and Written Opinion; Application No. PCT/US2008/075487; Mailing Date: Dec. 31, 2008, 7 pages.
International Search Report and Written Opinion; Application No. PCT/US2008/087527; Mailing Date: Jul. 30, 2009, 10 pages.
International Search Report and Written Opinion; Application No. PCT/US2009/031150; Mailing Date: Aug. 28, 2009, 6 pages.
International Search Report and Written Opinion; Application No. PCT/US2009/031710; Mailing Date: Sep. 1, 2009, 10 pages.
International Search Report and Written Opinion; Application No. PCT/US2009/036561; Mailing Date: Sep. 17, 2009, 12 pages.
Minns, R.J., et al., "Preliminary Design and Experimental Studies of a Noval Soft Implant for Correcting Sagittal Plane Instability in the Lumbar Spine," (1997) Spine, 22(16): 1819-1827.
Supplementary European Search Report; Application No. EP05849654.6; Applicant: Vertiflex, Inc.; Date of Completion: May 15, 2009, 10 pages.
Supplementary European Search Report; Application No. EP07861426.0; Applicant: Vertiflex, Inc.; Date of Completion: Jun. 7, 2011, 6 pages.
Supplementary European Search Report; Application No. EP07861721.4; Applicant: Vertiflex, Inc.; Date of Completion: Nov. 24, 2009, 6 pages.

(56) References Cited

OTHER PUBLICATIONS

Supplementary European Search Report; Application No. EP09170304.1; Applicant: Vertiflex, Inc.; Date of Completion: Nov. 11, 2009, 5 pages.
Supplementary European Search Report; Application No. EP09170338.9; Applicant: Vertiflex, Inc.; Date of Completion: Nov. 12, 2009, 6 pages.
Supplementary European Search Report; Application No. EP09702116.6; Applicant: Vertiflex, Inc.; Date of Completion: Feb. 11, 2011, 6 pages.
Supplementary European Search Report; Application No. EP11151901.3; Applicant: Vertiflex, Inc.; Date of Completion: Apr. 7, 2011, 6 pages.
Swan, Colby, "Preliminary Design and Experimental Studies of a Novel Soft Implant for Correcting Sogittal Plane Instability in the Lumbar Spine," Spine, 1997, 22(16), 1826-1827.
Supplementary European Search Report; Application No. EP05815519.3; Applicant: The Board of Trustees of Leland Stanford Junior University; Date of Completion: Sep. 28, 2011, 9 pages.
Supplementary European Search Report; Application No. EP05849654; Applicant: The Board of Trustees of Leland Stanford Junior University; Date of Completion: May 15, 2009, 5 pages.
Australia Exam Report for Application No. AU2006329867, Applicant: The Board of Trustees of Leland Stanford Junior University; Date of Issue: Jan. 27, 2012, 2 pages.
Australia Exam Report for Application No. AU2007317886, Applicant: VertiFlex, Inc.; Date of Issue: Jun. 18, 2012, 3 pages.
Australia Exam Report for Application No. AU2008241447, Applicant: VertiFlex, Inc.; Date of Issue: Jul. 5, 2012, 4 pages.
Australia Exam Report for Application No. AU2008275708, Applicant: VertiFlex, Inc.; Date of Issue: Nov. 12, 2012, 4 pages.
Australia Exam Report for Application No. AU2008279680, Applicant: VertiFlex, Inc.; Date of Issue: Oct. 30, 2012, 5 pages.
Australia Exam Report for Application No. AU2008296066, Applicant: VertiFlex, Inc.; Date of Issue: Mar. 6, 2013, 3 pages.
Australia Exam Report for Application No. AU2008343092, Applicant: VertiFlex, Inc.; Date of Issue: Feb. 8, 2013, 4 pages.
Australia Exam Report No. 2 for Application No. AU2009206098, Applicant: VertiFlex, Inc.; Date of Issue: Aug. 19, 2014, 4 pages.
Australia Exam Report No. 1 for Application No. AU2009206098, Applicant: VertiFlex, Inc.; Date of Issue: Mar. 6, 2013, 4 pages.
Canada Exam Report for Application No. CA2634251, Applicant: The Board of Trustees of Leland Stanford Junior University; Date of Issue: Dec. 3, 2013, 2 pages.
Canada Exam Report for Application No. CA2668833, Applicant: Vertiflex, Inc.; Date of Issue: Dec. 5, 2013, 2 pages.
Canada Exam Report for Application No. CA2695937, Applicant: Vertiflex, Inc.; Date of Issue: Aug. 7, 2014, 2 pages.
Canada Exam Report for Application No. CA2697628, Applicant: Vertiflex, Inc.; Date of Issue: Oct. 16, 2014, 2 pages.
Canada Exam Report for Application No. CA2698718, Applicant: Vertiflex, Inc.; Date of Issue: May 20, 2014, 3 pages.
Supplementary European Search Report; Application No. EP06845480; Applicant: VertiFlex, Inc.; Date of Completion: Aug. 14, 2012, 9 pages.
Supplementary European Search Report for Application No. EP13184922.6; Applicant: VertiFlex, Inc.; Date of Issue: Oct. 30, 2013, 8 pages.
Supplementary European Search Report for Application No. EP07861426; Applicant: VertiFlex, Inc.; Date of Issue: Jun. 7, 2011, 6 pages.
Supplementary European Search Report for Application No. EP07861721.4; Applicant: VertiFlex, Inc.; Date of Issue: Nov. 24, 2009, 6 pages.
Supplementary European Search Report for Application No. EP09170304.1; Applicant: VertiFlex, Inc.; Date of Issue: Nov. 24, 2009, 5 pages.
Supplementary European Search Report for Application No. EP09170338.9; Applicant: VertiFlex, Inc.; Date of Issue: Nov. 24, 2009, 6 pages.
Supplementary European Search Report for Application No. EP11151901.3; Applicant: VertiFlex, Inc.; Date of Issue: Apr. 7, 2011, 6 pages.
Supplementary European Search Report for Application No. EP08742949.4; Applicant: VertiFlex, Inc.; Date of Issue: Sep. 17, 2012, 6 pages.
Supplementary European Search Report for Application No. EP08780034.8; Applicant: VertiFlex, Inc.; Date of Issue: Sep. 19, 2012, 7 pages.
Supplementary European Search Report for Application No. EP08794704.0; Applicant: VertiFlex, Inc.; Date of Issue: Oct. 23, 2012, 9 pages.
Supplementary European Search Report for Application No. EP08799267.3; Applicant: VertiFlex, Inc.; Date of Issue: Jun. 29, 2011, 7 pages.
Supplementary European Search Report for Application No. EP08867282.9; Applicant: VertiFlex, Inc.; Date of Issue: Nov. 28, 2012, 10 pages.
Supplementary European Search Report for Application No. EP09702116.6; Applicant: VertiFlex, Inc.; Date of Issue: Feb. 11, 2011, 7 pages.
International Search Report and Written Opinion; Application No. PCT/US2010/060498; Mailing Date: Aug. 25, 2011, 17 pages.
Australia Exam Report for Application No. AU2009223607, Applicant: VertiFlex, Inc.; Date of Issue: Jun. 4, 2013, 3 pages.
Australia Exam Report for Application No. AU2013273815, Applicant: The Board of Trustees of Leland Stanford Junior University; Date of Issue: Apr. 17, 2015, 3 pages.
International Search Report, counterpart PCT Application PCT/US2013/038534, Applicant: Vertiflex, Inc., Aug. 7, 2013, 16 pages.
McCulloch, John A., Young, Paul H., "Essentials of Spinal Microsurgery," 1998, pp. 453-485. Lippincott-Raven Publishers, Philadelphia, PA (37 pages total).
Lee, Seungcheol et al., "New Surgical Techniques of Percutaneous Endoscopic Lumbar Disectomy for Migrated Disc Herniation," Joint Dis. Rel. Surg., 16(2); pp. 102-110 (2005).
Choi, Gun et al., "Percutaneous Endoscopic Interlaminar Disectomy for Intracanalicular Disc Herniations at L5-S1 Using a Rigid Working Channel Endoscope," Operative Neurosurg., 58: pp. 59-68 (2006).
Lee, Seungcheol et al., "Percutaneous Endoscopic Interlaminar Disectomy for L5-S1 Disc Herniation: Axillary Approach and Preliminary Results," J. of Korean Neurosurg. Soc., 40: pp. 19-83 (2006).
Vertos mild Devices Kit—PRT-00430-C—Instructions for Use (13 pages total); see http://vertosmed.com/docs/mildIFU_PRT-00430-C.pdf., 2012.
Decision on Petition in U.S. Appl. No. 60/592,099, May 4, 2005.
Vaccaro, Alexander J. et al., MasterCases Spine Surgery, 2001, pp. 100-107. Thieme Medical Publishers, Inc., NY. (10 pages total).
Tredway, Trent L. et al., "Minimally Invasive Transforaminal Lumbar Interbody Fusion (MI-TLIF) and Lateral Mass Fusion with the MetRx System," (14 pages total), 2005.
Fast, Avital et al., "Surgical Treatment of Lumbar Spinal Stenosis in the Elderly," Arch Phys. Med Rehabil., Mar. 1985, pp. 149-151, vol. 66.
Palmer, Sylvain et al., "Bilateral decompressive surgery in lumbar spinal stenosis associated with spondylolisthesis: unilateral approach and use of a microscope and tubular retractor system," Neurosurgery Focus, Jul. 2002, pp. 1-6, vol. 13.
International Search Report and Written Opinion; Application No. PCT/US2009/029537; Applicant: Vertiflex, Inc. Mailing Date: Aug. 3, 2015, 14 pages.
European Extended Search Report Application No. EP13780608.9; Applicant: VertiFlex, Inc.; Date of Mailing: Nov. 23, 2015, 8 pages.

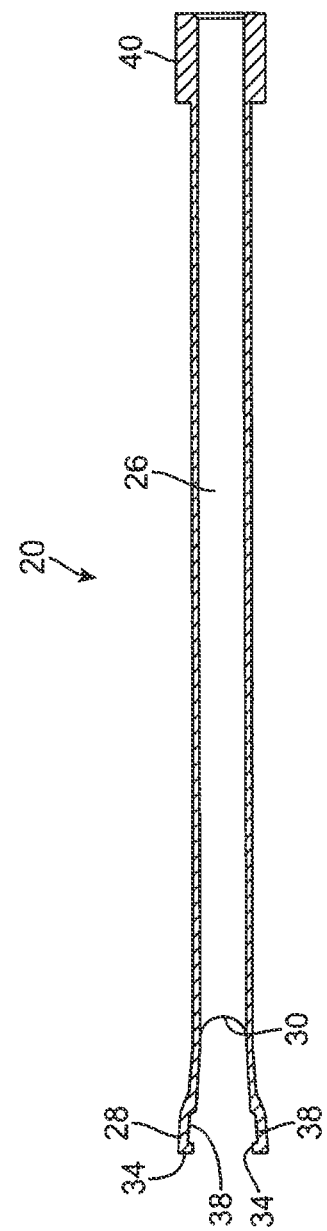

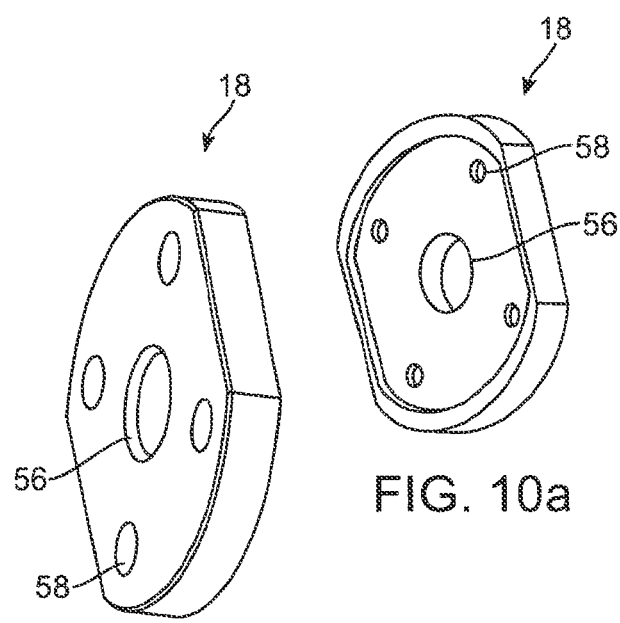

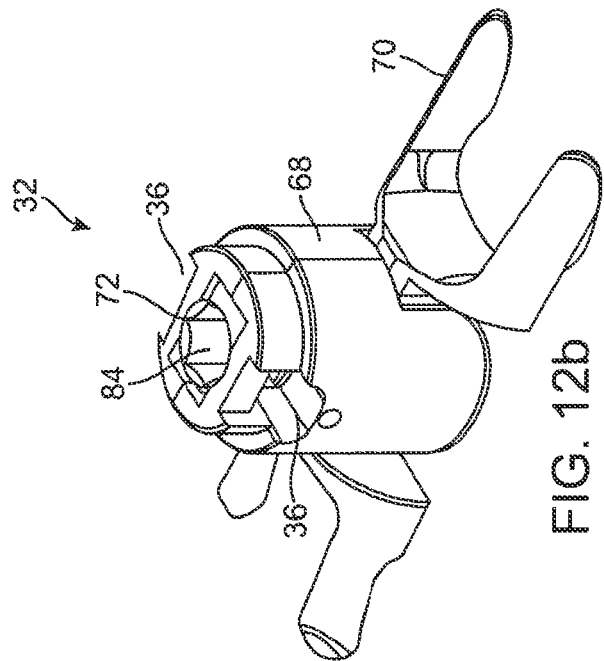
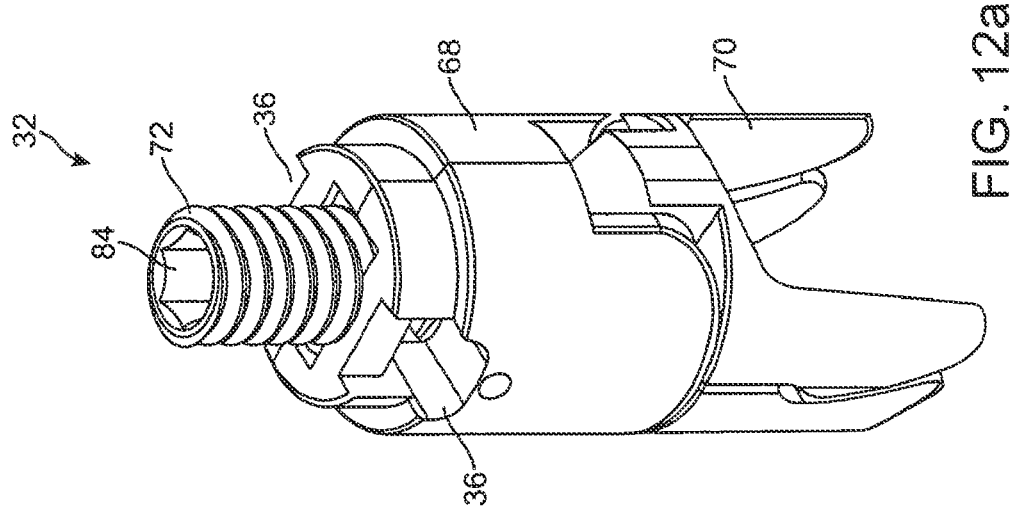

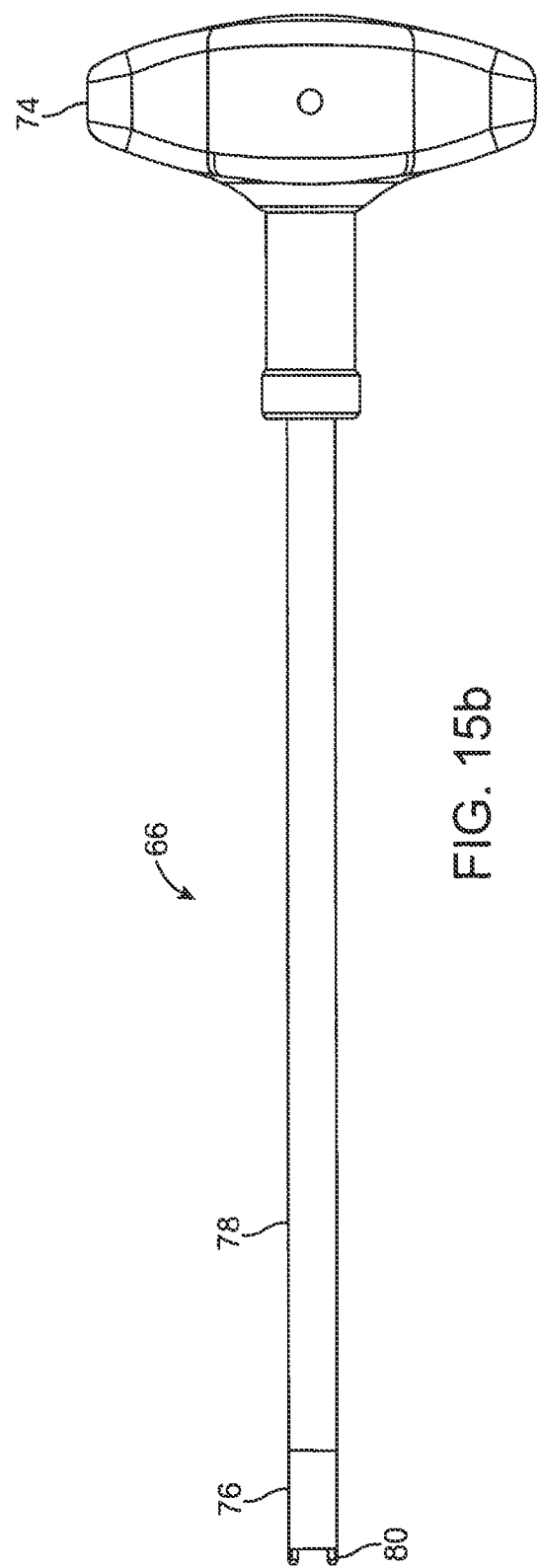

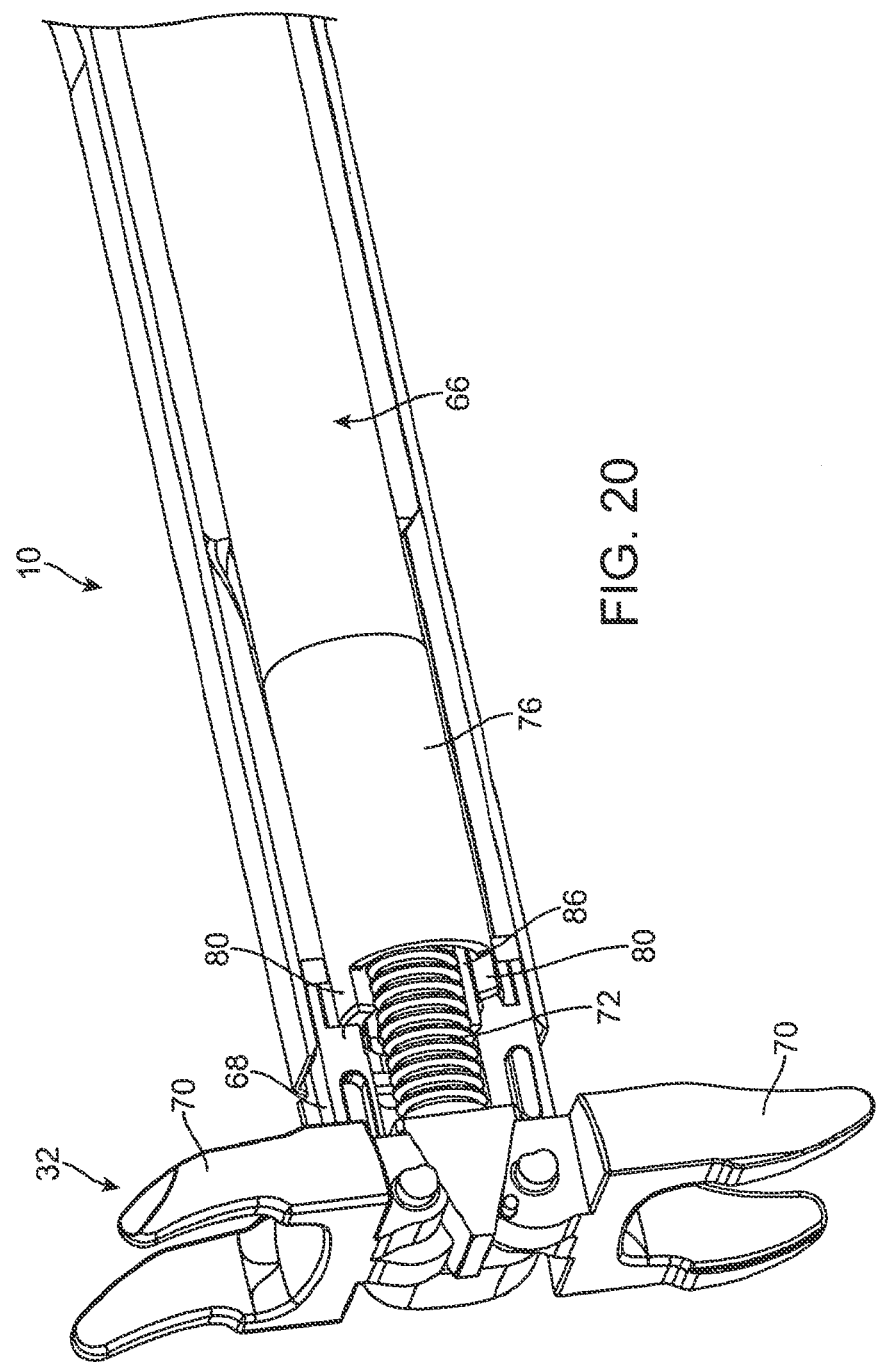

SPACER INSERTION INSTRUMENT

CROSS-REFERENCE TO RELATED APPLICATIONS

This application is a continuation of U.S. patent application Ser. No. 12/338,793, now U.S. Pat. No. 8,613,747, filed Dec. 18, 2008, now allowed, which claims priority to and the benefit of U.S. Provisional Patent Application No. 61/008,418 entitled "Spacer Insertion Instrument" filed on Dec. 19, 2007, which also claims priority to and is a continuation-in-part of U.S. patent application Ser. No. 12/205,511, now U.S. Pat. No. 8,123,782, filed on Sep. 5, 2008, entitled "Interspinous Spacer," which is a non-provisional of U.S. Provisional Patent Application No. 60/967,805, filed on Sep. 7, 2007, and entitled "Interspinous Spacer," and is a continuation-in-part of U.S. patent application Ser. No. 12/220,427, now U.S. Pat. No. 8,277,488, filed Jul. 24, 2008 and entitled "Interspinous Spacer," which is a non-provisional of U.S. Provisional Patent Application No. 60/961,741, filed Jul. 27, 2007, and entitled "Insterspinous Spacer," and is a continuation-in-part of U.S. patent application Ser. No. 12/217,662, now U.S. Pat. No. 8,273,108, filed Jul. 8, 2008, and entitled "Interspinous Spacer," which is a non-provisional of U.S. Provisional Patent Application No. 60/958,876, filed Jul. 9, 2007, and entitled "Interspinous Spacer," and is a continuation-in-part of U.S. patent application Ser. No. 12/148,104, now U.S. Pat. No. 8,292,922, filed Apr. 16, 2008, and entitled "Interspinous Spacer," which is a non-provisional of U.S. Provisional Patent Application No. 60/923,971, filed on Apr. 17, 2007, and entitled "Interspinous Spacer," and U.S. Provisional Patent Application No. 60/923,841, filed Apr. 16, 2007, entitled "Spacer Insertion Instrument," all of which are hereby incorporated by reference in their entireties. Patent application Ser. No. 12/338,793 is also a continuation-in-part of U.S. Patent application Ser. No. 11/593,995, now U.S. Pat. No. 8,425,559, filed on Nov. 7, 2006, entitled "Systems and Methods for Posterior Dynamic Stabilization of the Spine," and a continuation-in-part of U.S. patent application Ser. No. 11/582,874, now U.S. Pat. No. 8,128,662, filed on Oct. 18, 2006, and entitled "Minimally Invasive Tooling for Delivery of Interspinous Spacer" and a continuation-in-part of U.S. patent application Ser. No. 11/314,712, now U.S. Pat. No. 8,152,837, filed on Dec. 20, 2005 and entitled "Systems and Methods for Posterior Dynamic Stabilization of the Spine," and a continuation-in-part of U.S. patent application Ser. No. 11/190,496, now U.S. Pat. No. 8,409,282, filed Jul. 26, 2005, and entitled "Systems and Methods for Posterior Dynamic Stabilization of the Spine," and a continuation-in-part of U.S. patent application Ser. No. 11/079,006, now U.S. Pat. No. 8,012,207, filed on Mar. 10, 2005, and entitled "Systems and Methods for Posterior Dynamic Stabilization of the Spine," which is a continuation-in-part of U.S. patent application Ser. No. 11/052,002, now U.S. Pat. No. 8,317,864, filed Feb. 4, 2005, entitled "Systems and Methods for Posterior Dynamic Stabilization of the Spine," which is a continuation-in-part of U.S. patent application Ser. No. 11/006,502, now U.S. Pat. No. 8,123,807, filed on Dec. 6, 2004, and entitled "Systems and Methods for Posterior Dynamic Stabilization of the Spine" which is a continuation-in-part of U.S. patent application Ser. No. 10/970,843, now U.S. Pat. No. 8,167,944, filed Oct. 20, 2004, and entitled "Systems and Methods for Posterior Dynamic Stabilization of the Spine," all of which are hereby incorporated by reference in their entireties.

FIELD

The present invention generally relates to medical devices for the spine. In particular, the present invention relates to minimally invasive instruments for delivery of an implant between adjacent spinous processes of a patient's spine.

BACKGROUND

With spinal stenosis, the spinal canal narrows and pinches the spinal cord and nerves, causing pain in the back and legs. Typically, with age, a person's ligaments may thicken, intervertebral discs may deteriorate and facet joints may break down all contributing to the condition of the spine characterized by a narrowing of the spinal canal. Injury, heredity, arthritis, changes in blood flow and other causes may also contribute to spinal stenosis.

Doctors have been at the forefront with various treatments of the spine including medications, surgical techniques and implantable devices that alleviate and substantially reduce debilitating pain associated with the back. In one surgical technique, a spacer is implanted between adjacent spinous processes of a patient's spine. The implanted spacer opens the spinal canal, maintains the desired distance between vertebral body segments, and as a result, avoids impingement of nerves and relieves pain. For suitable candidates, an implantable interspinous spacer may provide significant benefits in terms of pain relief.

Any surgery is an ordeal. However, the type of device and how it is implanted has an impact. For example, one consideration when performing surgery to implant an interspinous spacer is the size of the incision that is required to allow introduction of the device. Small incisions and minimally invasive techniques are generally preferred as they affect less tissue and result in speedier recovery times. As such, there is a need for interspinous process spacers and instruments that deliver them that work well with surgical techniques that are minimally invasive for the patient. The present invention sets forth such an instrument.

SUMMARY

According to one aspect of the invention, an instrument is provided. The instrument includes a handle connected to a first assembly. The first assembly comprises an outer shaft. An inner shaft is located inside the outer shaft and configured for relative translational motion with respect to the outer shaft. A control is configured to effect the relative translational motion wherein the relative translational motion causes one of the outer or inner shafts to move with respect to the other and thereby deflect at least one prong formed on one of the inner or outer shafts. Such deflection causes connection or engagement with a juxtapositioned spacer. A driver having a distal portion configured to reversibly arrange the spacer between and including at least one deployed configuration and at least one undeployed configuration.

According to another aspect of the invention, an instrument having a longitudinal axis and connectable to a spacer is provided. The instrument comprises a substantially radiolucent portion connected to a substantially non-radiolucent portion. The substantially non-radiolucent portion has a radiographic projection on a plane perpendicular to the longitudinal axis that is substantially coincident with a radiographic or non-radiographic projection of a connected undeployed spacer on said plane.

According to another aspect of the invention, a method is disclosed. The method includes the step of connecting an interspinous spacer to a distal end of an instrument. The connected interspinous spacer is inserted into an interspinous space of a patient's spine with the instrument. The interspinous spacer is arranged by the instrument into at least one deployed configuration while the interspinous spacer is inserted in the interspinous space. The interspinous spacer is disconnected from the instrument leaving the interspinous spacer located in the interspinous space.

According to another aspect of the invention, a method is disclosed. The method includes the step of inserting a distal end of an instrument into an interspinous space of a patient's spine. The distal end of the instrument is connected to an interspinous spacer implanted in the interspinous space. The interspinous spacer is arranged with said instrument into at least one undeployed configuration while said instrument is inserted in the interspinous space and connected to the interspinous spacer. The connected interspinous spacer is removed from the patient with the instrument.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 7 illustrates a cross-sectional view of an inner shaft of a spacer insertion instrument according to the present invention.

FIG. 10a illustrates a perspective view of a proximal end cap of a spacer insertion instrument according to the present invention.

FIG. 10b illustrates a perspective view of a proximal end cap of a spacer insertion instrument according to the present invention.

FIG. 12a illustrates a perspective view of a spacer in an undeployed configuration.

FIG. 12b illustrates a perspective view of a spacer in a deployed configuration.

FIG. 15b illustrates a side view of a driving tool according to the present invention.

FIG. 20 illustrates a partial cross-sectional view of a spacer insertion instrument and driving tool connected to a spacer in a deployed configuration according to the present invention.

DETAILED DESCRIPTION

Figure 15A:
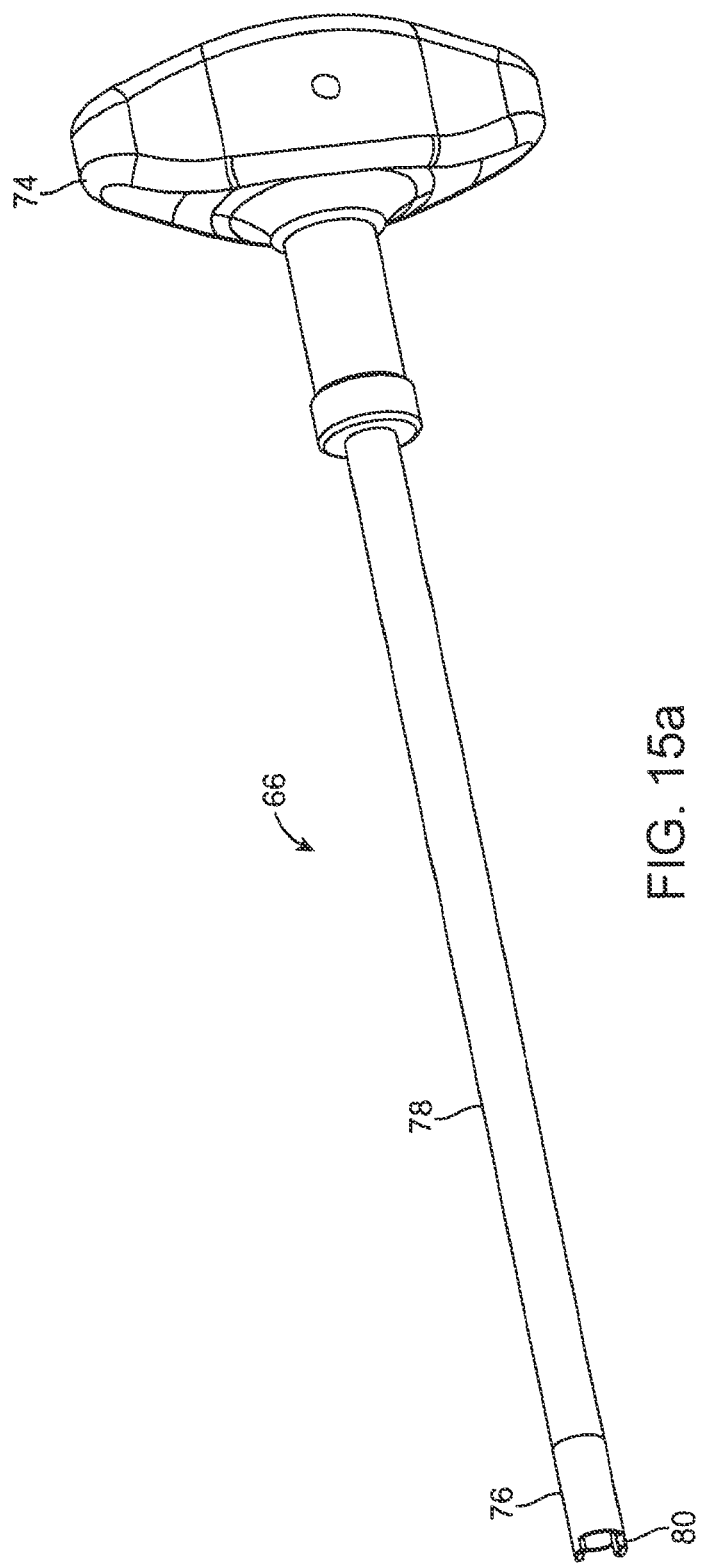
FIG. 15a illustrates a perspective view of a driving tool according to the present invention.
Figure 15C:
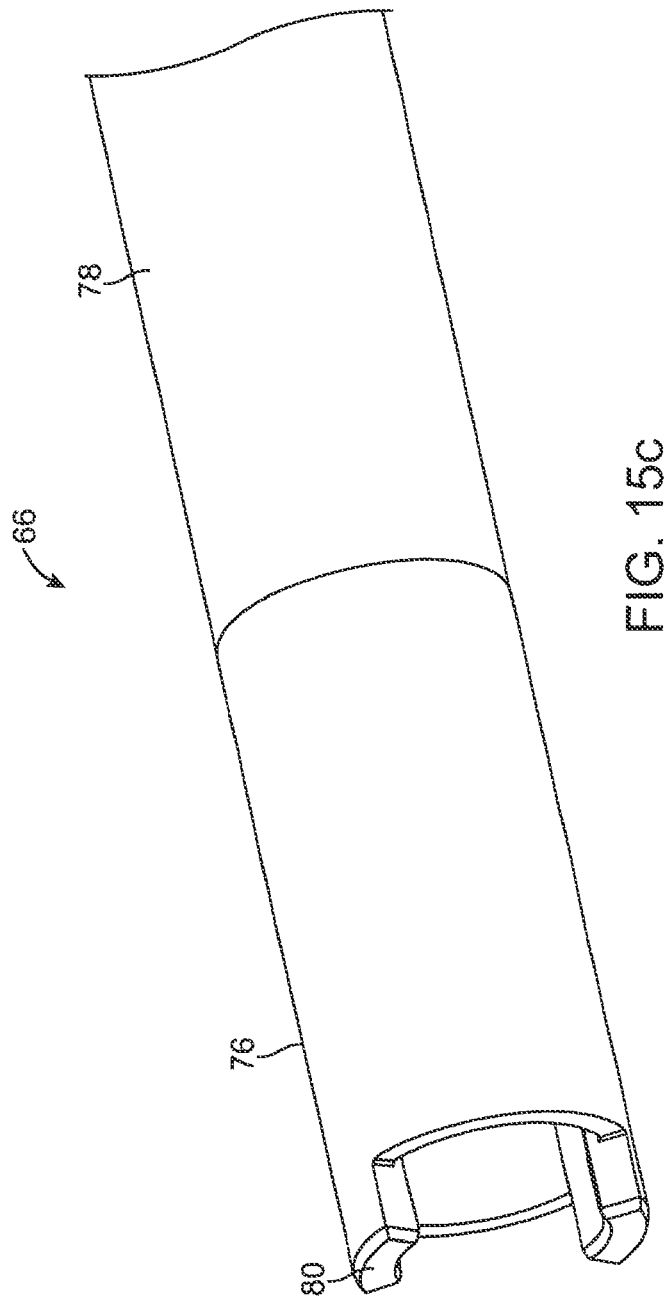
FIG. 15c illustrates a partial perspective view of a driving tool according to the present invention.
Figure 16:
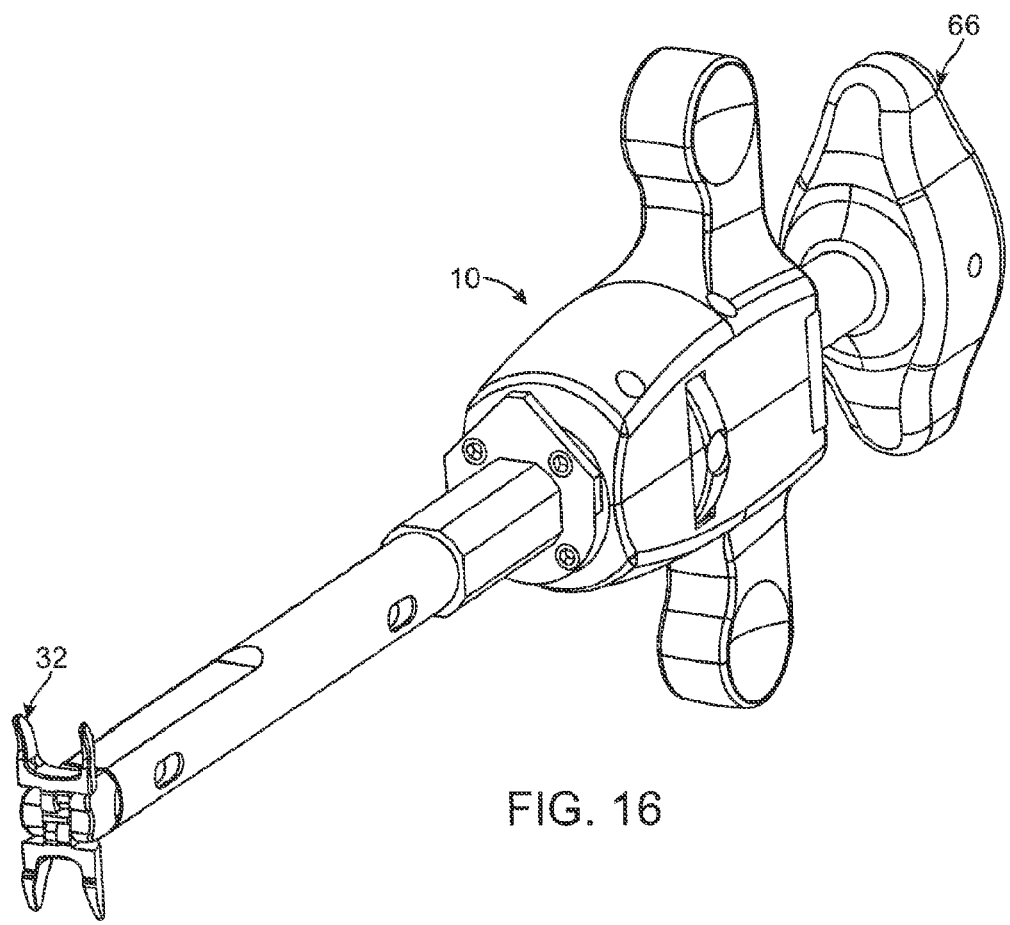
FIG. 16 illustrates a perspective view of a spacer insertion instrument and driving tool connected to a spacer in a deployed configuration according to the present invention.
Figure 17:
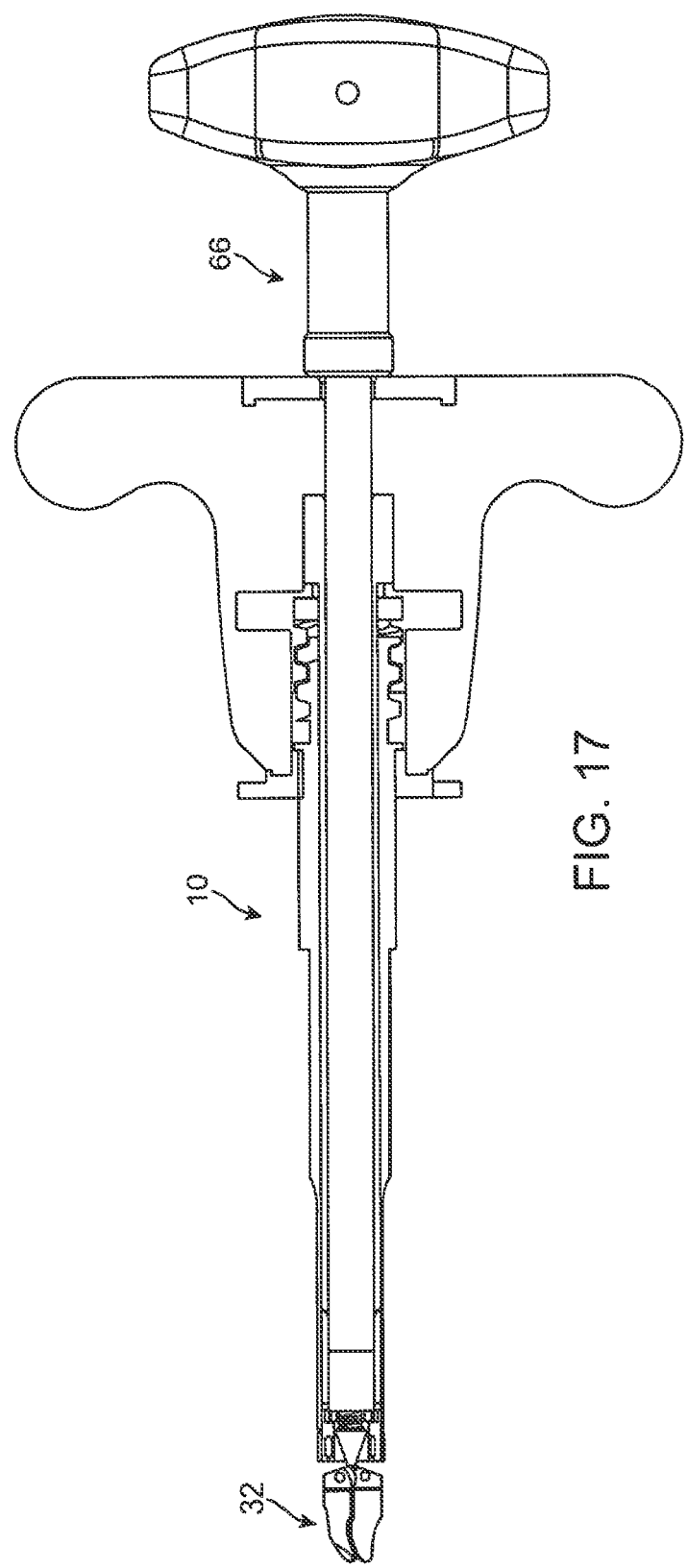
FIG. 17 illustrates a cross-sectional view of a spacer insertion instrument and driving tool connected to a spacer in an undeployed configuration according to the present invention.

Turning to FIGS. 1-6, there is shown a spacer insertion instrument 10 according to the present invention. The spacer insertion instrument 10 includes a first assembly 12 connected to a handle assembly 14 and retained by a distal end cap 16 and a proximal end cap 18. The instrument 10 also includes a driving tool 66 that is removably insertable into the central passageway of the instrument 10. FIGS. 15a, 15b and 15c illustrate the driving tool 66 and FIG. 16 shows the instrument 10 with the driving tool 66 inserted.

Still referencing FIGS. 1-6, the first assembly 12 of the insertion instrument 10 is configured to releasably clamp to a body of an interspinous process implant to be delivered into or removed from a patient using the instrument 10. The first assembly 12 includes an inner shaft 20, an outer shaft 22 and a control 24. The inner shaft 20 is connected to the handle assembly 14 and the outer shaft 22 is passed over the inner shaft 20 and allowed to translate with respect thereto by means of a control 24 that is threadingly engaged with the outer shaft 22. With rotation of the control 24 in either direction, the outer shaft 22 translates with respect to the stationary inner shaft 20. In another variation of the invention, the outer shaft 22 is connected to handle assembly 14 and the inner shaft 20 is threadingly engaged with the control 24 such that rotation of the control 24 moves the inner shaft 20 with respect to the outer shaft 22. Although rotation of the control 24 is used in one variation, other variations are within the scope of the present invention such as, for example, translation of the control 24 or movement of the outer shaft 22 relative to the inner shaft 20.

Turning now to FIG. 7, there is shown an inner shaft 20 according to the present invention. As seen in the drawings, the inner shaft 20 is substantially cylindrical in shape having a central bore 26 extending from end to end. The distal end of the inner shaft 20 includes a pair of prongs 28 with each prong being substantially oppositely located from each other. The finger-like prongs 28 are formed by openings 30 extending proximally from the distal end. The fingers are flexible and, when in a normal position, splay slightly outwardly from the longitudinal axis as shown in FIG. 7. The prongs 28 are configured to connect with a spacer 32 of the like shown in FIGS. 12-14 or other similar spacers. In particular, the prongs 28 include extensions 34 that extend inwardly toward the longitudinal axis in a hook-like fashion. These extensions 34 are configured to be inserted into prong-receiving portions 36 (see FIGS. 12-14) on the spacer 32 and securely clamp thereto. The prongs 28 also include conforming surfaces 38 configured to conform to the spacer 32 in a manner best suited for secure attachment thereto. The proximal end of the inner shaft 20 includes a proximal portion 40 having a larger cross section and configured for insertion into a conformingly shaped recess in the handle assembly 14.

Turning now to FIGS. 8a-8d, there is shown the outer shaft 22 of the first assembly 12. As seen in the drawings, the outer shaft 22 is substantially cylindrical in shape having a central bore 42 extending from end to end. The outer shaft 22 is sized such that the inner shaft 20 fits inside the outer shaft 22. The distal end includes a pair of flattened portions 44 located substantially opposite from each other. There is a middle portion 46 having a larger cross-section and a threaded proximal portion 48. The threaded proximal portion 48 is configured for threaded connection with the control 24. In one variation, the middle portion 46 includes features such as an octagonal shape as seen in FIG. 16 that serve to align the instrument 10 when inserted into a cannula positioned to an interspinous space of a patient. The features on the middle portion 46 are aligned with similar complementary features on a cannula so that insertion of the instrument into the cannula is limited by the alignment of the features with the result being proper orientation of the instrument relative to the cannula and in turn relative to the patient. The outer shaft 22 includes at least one aperture formed in the sidewall of the shaft to provide access to the inner shaft and the interior of the shaft construct for cleaning purposes.

Figure 9A:
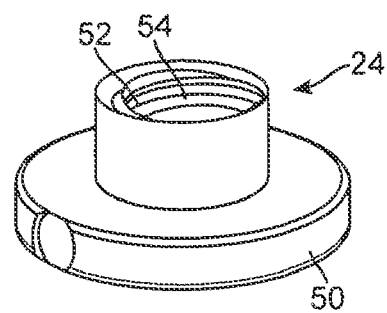
FIG. 9a illustrates a perspective view of a control of a spacer insertion instrument according to the present invention.
Figure 9B:
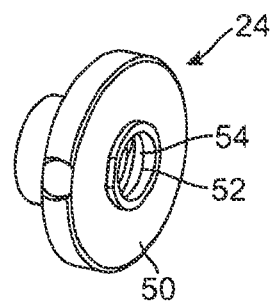
FIG. 9b illustrates a perspective view of a control of a spacer insertion instrument according to the present invention.
Figure 9C:
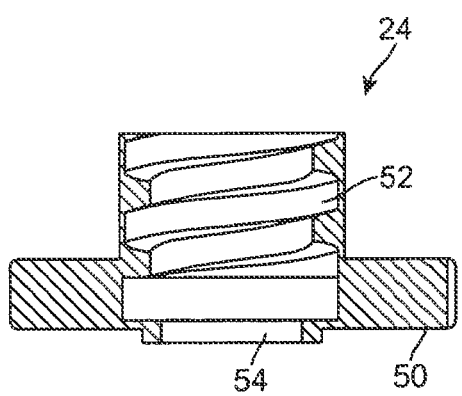
FIG. 9c illustrates a cross-sectional view of a control of a spacer insertion instrument according to the present invention.

Turning now to FIGS. 9a-9c, there is shown the control 24 of the first assembly 12. The control 24 includes a user interface such as a finger portion or grip 50. In the variation shown in FIGS. 9a-9c, the user interface 50 is an outer circular or disk shaped portion for easily effecting rotation of the control 24 with a thumb or index finger. The control 24 also includes a connecting portion 52 that connects the control 24 to effect relative translation of the inner shaft 20 with respect to the outer shaft 22. In particular, in the variation shown in the drawings, the connecting portion 52 is a cylindrical portion connected to the user interface 50. The cylindrical portion has a threaded inner surface for engaging the threaded proximal portion 48 of the outer shaft 22 wherein the outer shaft 22 is received inside a threaded bore 54 of the connecting portion 52.

Turning now to FIGS. 10a and 10b, there is shown the proximal end cap 18 of the present invention. The end cap 18 is configured to cap the proximal end of the handle assembly 14. The handle assembly 14, if made of multiple parts, is held together, in part, by the end cap 18, capturing at least a portion of the first assembly 12 therein. The end cap 18 includes a central bore 56 providing a passage through the instrument 10 end to end. Also, apertures 58 are formed in the end cap 18 for receiving fasteners (not shown) therein for attachment to the handle assembly 14.

Figure 1:
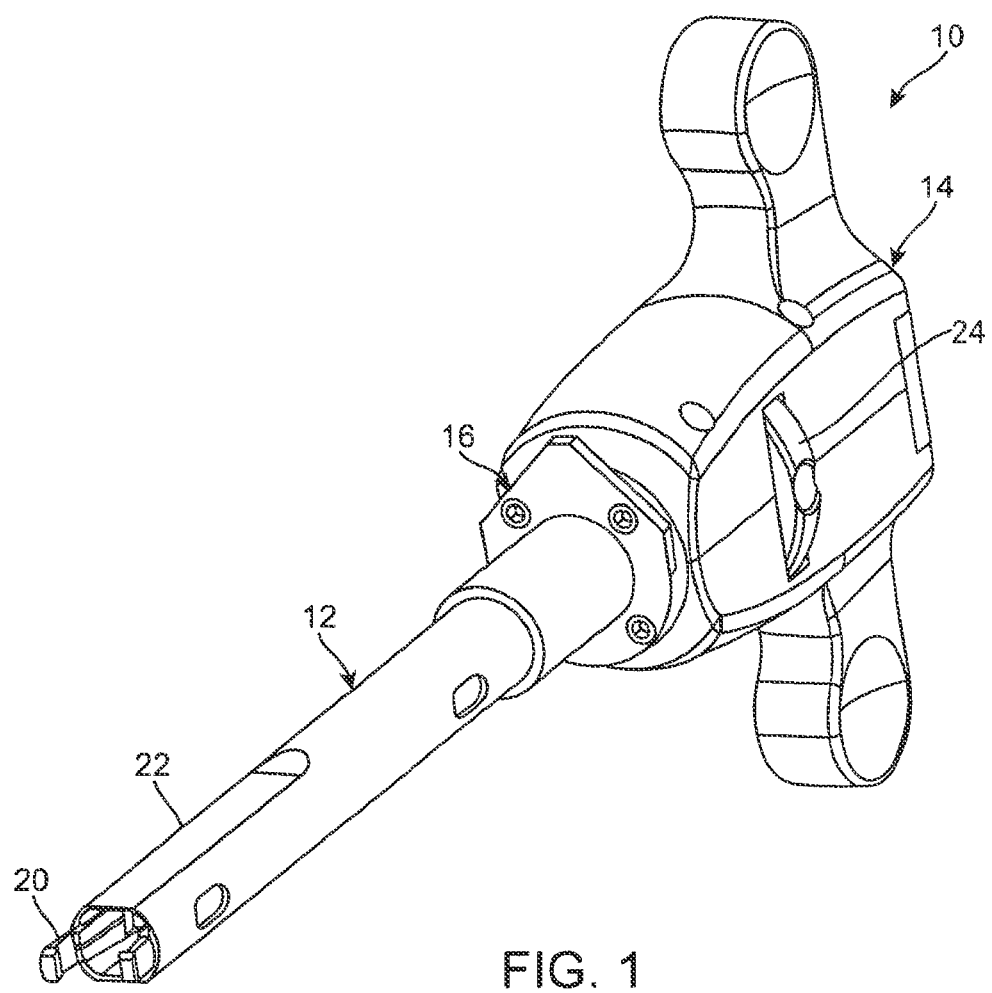
FIG. 1 illustrates a perspective view of a spacer insertion instrument without a driving tool according to the present invention.
Figure 2:
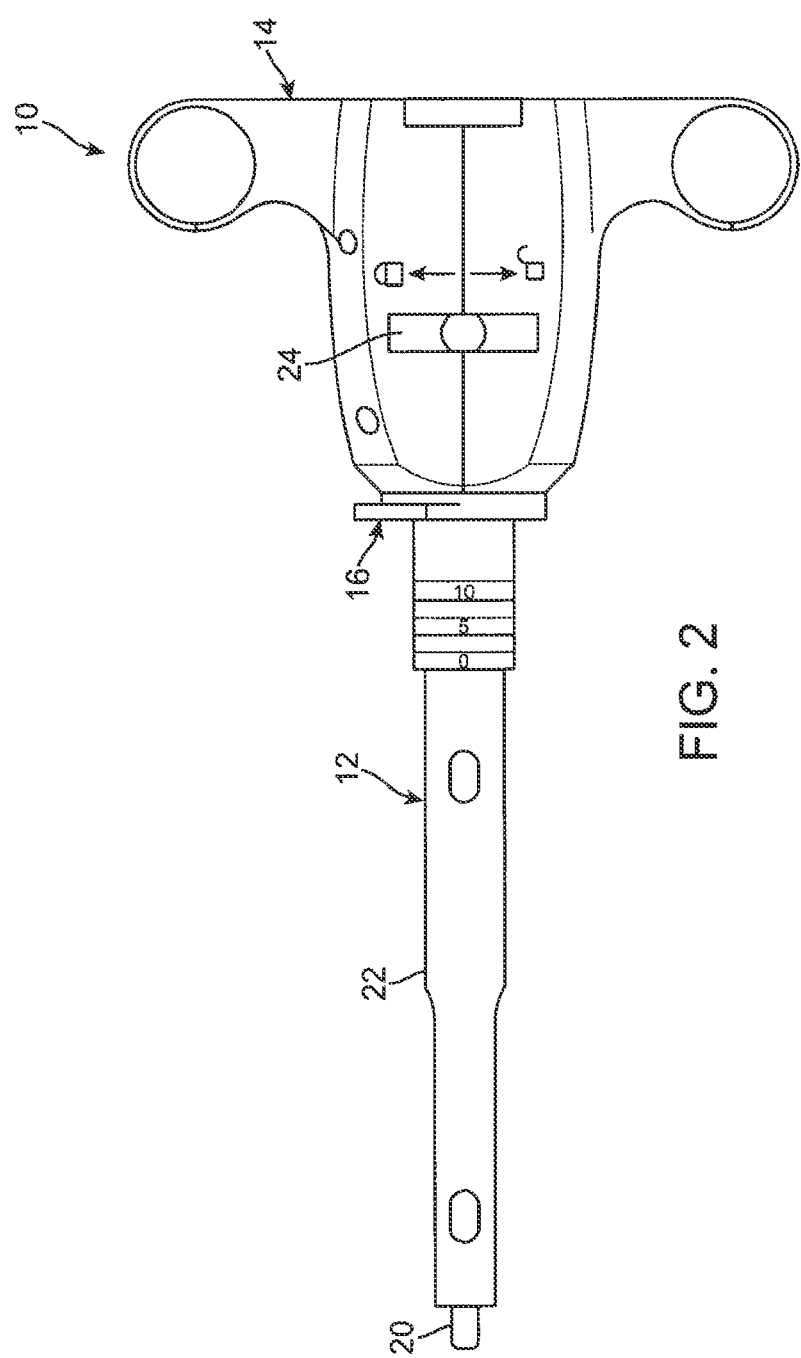
FIG. 2 illustrates a side view of a spacer insertion instrument without a driving tool according to the present invention.
Figure 4:
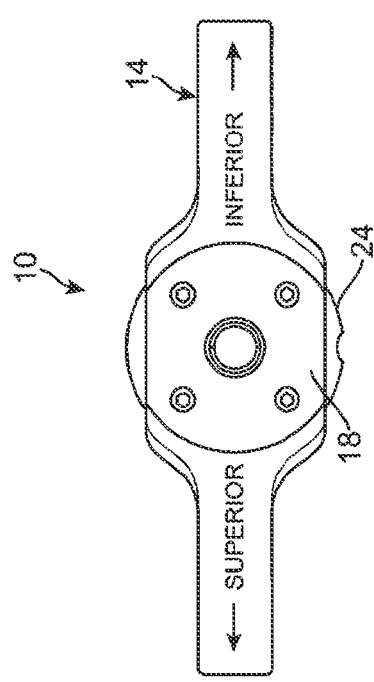
FIG. 4 illustrates an end view of a spacer insertion instrument without a driving tool according to the present invention.
Figure 5:
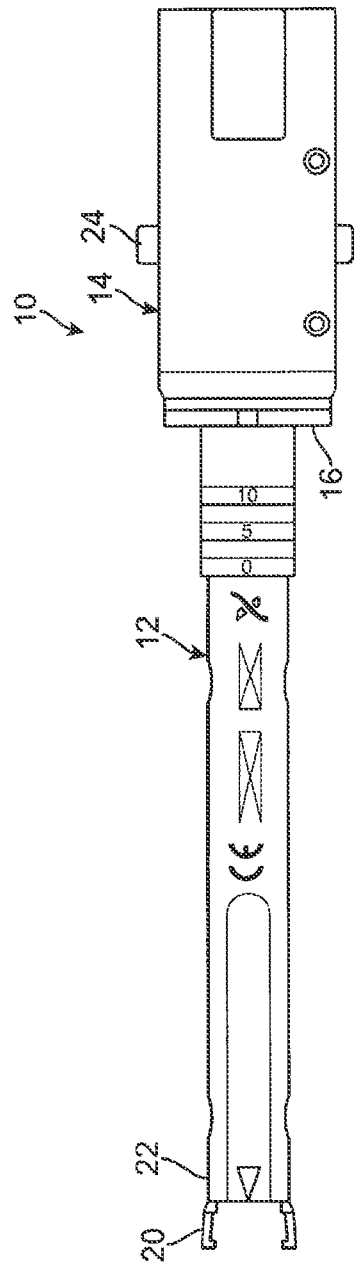
FIG. 5 illustrates a top view of a spacer insertion instrument without a driving tool according to the present invention.
Figure 3:
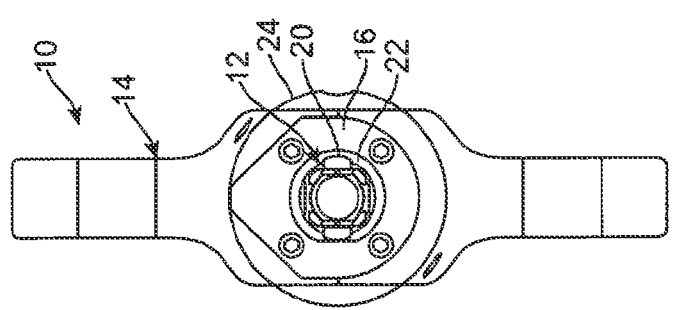
FIG. 3 illustrates a front view of a spacer insertion instrument without a driving tool according to the present invention.
Figure 11:
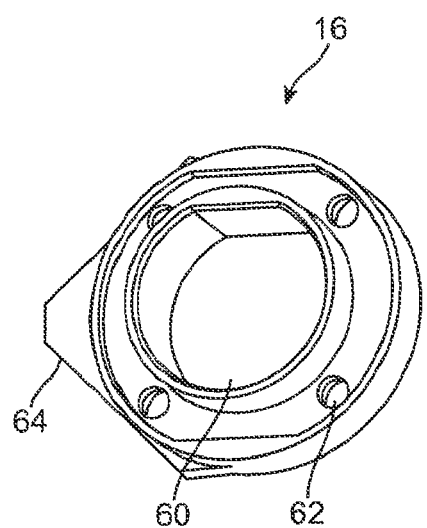
FIG. 11 illustrates a perspective view of a distal end cap of a spacer insertion instrument according to the present invention.

Turning now to FIG. 11, there is shown the distal end cap 16 of the present invention. The end cap 16 is configured to cap the distal end of the handle assembly 14. The handle assembly 14, if made of multiple parts, is held together, in part, by the distal end cap 16, capturing at least a portion of the first assembly 12 therein. The distal end cap 16 includes a central bore 60 sized to receive the outer shaft 22 therein. Also, apertures 62 are formed in the end cap 16 for receiving fasteners (not shown) therein for attachment to the handle assembly 14. In one variation, the distal end cap 16 has a directional indicator 64 in the shape of an arrow indicating, for example, a direction information such as "cephalad" as shown in FIG. 3 to help the surgeon to easily orientate the instrument 10.

Figure 6:
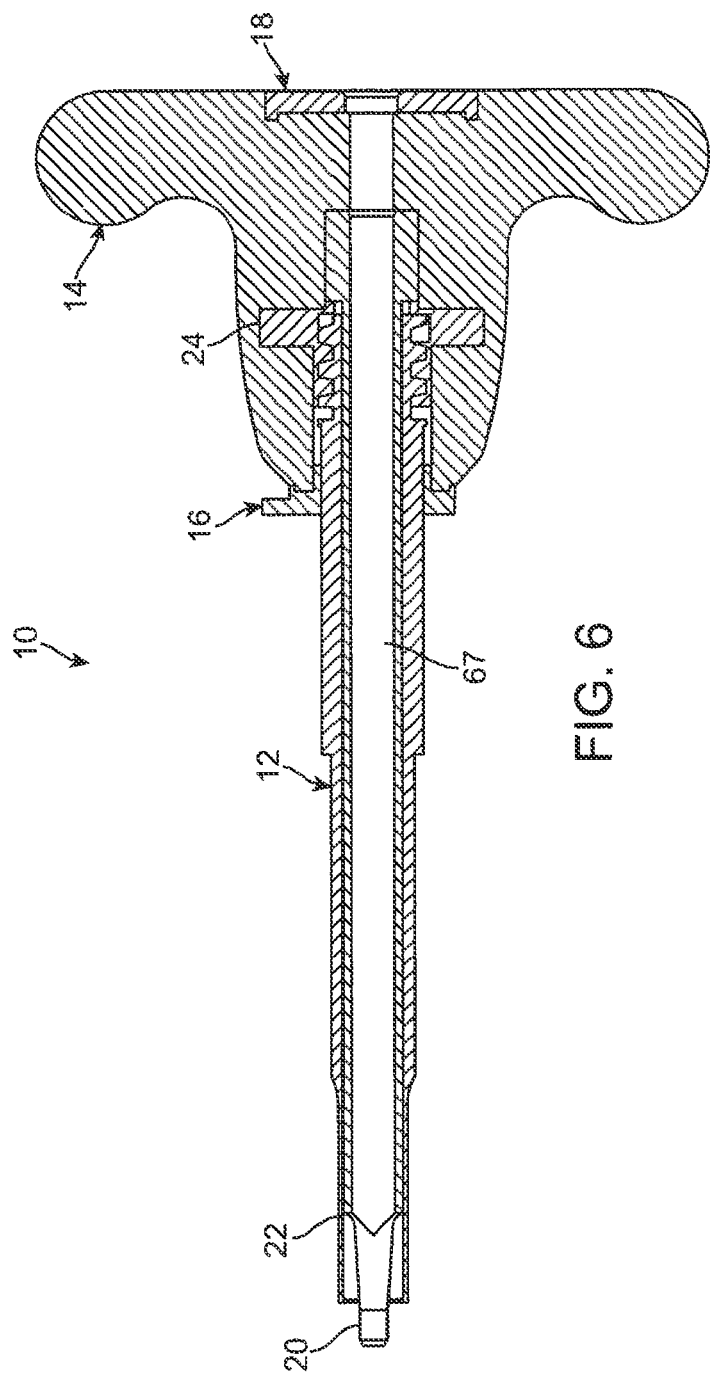
FIG. 6 illustrates a cross-sectional view of a spacer insertion instrument without a driving tool according to the present invention.
Figure 8A:
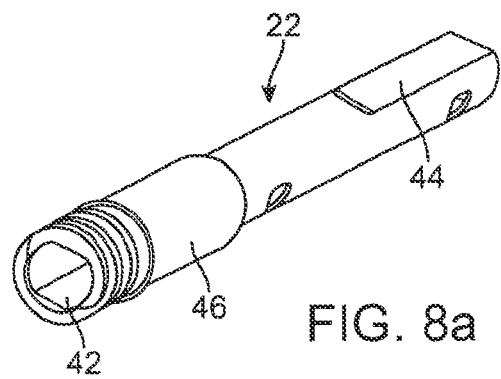
FIG. 8a illustrates a perspective view of an outer shaft of a spacer insertion instrument according to the present invention.
Figure 8B:
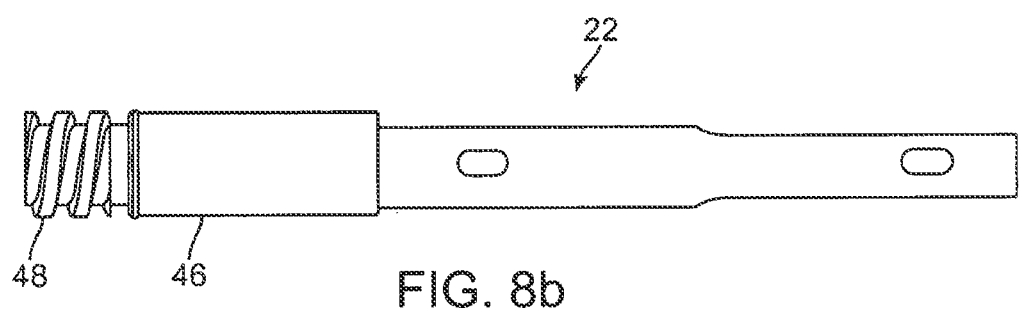
FIG. 8b illustrates a side view of an outer shaft of a spacer insertion instrument according to the present invention.
Figure 8C:
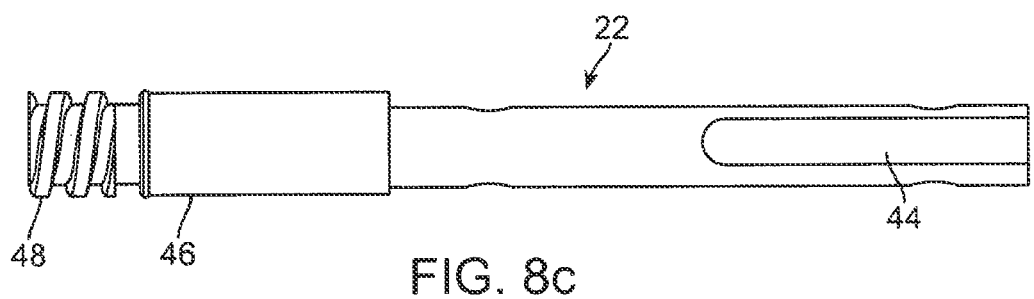
FIG. 8c illustrates a side view of an outer shaft of a spacer insertion instrument according to the present invention.
Figure 8D:
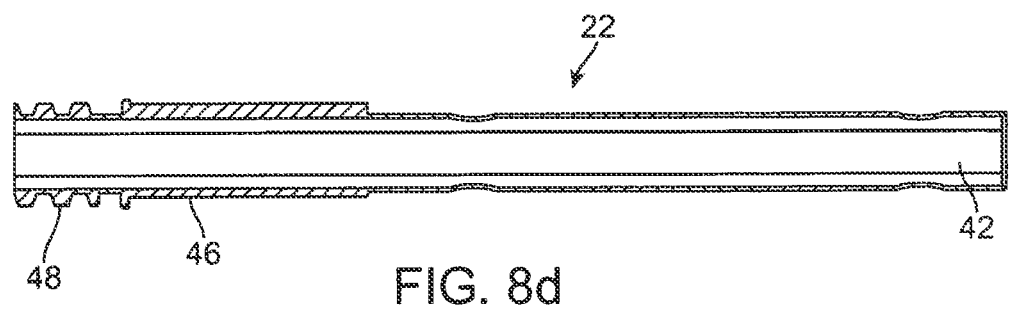
FIG. 8d illustrates a cross-sectional view of an outer shaft of a spacer insertion instrument according to the present invention.

The assembly of the spacer insertion instrument 10 will now be described. With particular reference back to FIG. 6, the control 24 is threaded onto the threaded proximal portion 48 of the outer shaft 22. The prongs 28 of the inner shaft 20 are compressed together slightly and the inner shaft 20 is inserted into the outer shaft 22. The first assembly 12 is then placed inside first assembly receiving portions of the handle assembly 14 and if more than one piece comprises the handle assembly 14 as, for example, in a clam shell construction, the handle assembly 14 is joined and secured together by the distal and proximal end caps 14, 16 fastened to the handle assembly 14. Additional fastening elements such as fasteners, screws, glue and the like may also be additionally or alternatively employed to capture at least a portion of and secure the first assembly 12 inside the handle assembly 14. With the instrument 10 assembled, there is a central passageway 67 clearly visible in the cross-sectional view of the instrument 10 shown in FIG. 6. The central passageway 67 extends from one end to the other end of the instrument 10. Through this central passageway 67, the driving tool 66 is removably inserted to deploy or undeploy the interspinous spacer. FIG. 16 illustrates a driving tool 66 inserted into the instrument 10 and engaged with a spacer 32 in a deployed configuration.

Jumping now to FIGS. 15a, 15b and 15c, there is shown a driving tool 66 according to the present invention. The driving tool 66 includes a handle 74 at the proximal end and a spacer engaging bit 76 at the distal end. The handle 74 and bit 76 are interconnected by a middle shaft portion 78. The driving tool 66 is configured and sized to be inserted into the central passageway 67 of the instrument 10 such that the bit 76 at the distal end operatively connects with a spacer loaded and locked into the prongs 28 of the instrument 10. The distal bit 78 includes features 80 for engaging with the operative portion of the spacer 32 in order to effect deployment or undeployment of the spacer 32. A driving tool 66 may have a different distal bit 76 in order to mate with a complementarily different member on the spacer. For example, the driving tool 66 shown in FIG. 15 includes features 80 comprising two oppositely located projections which are configured to mate with complementary features on the spacer. In another variation of the driving tool 66, the distal bit 66 may simply be a hexagonally shaped or other polygonal shaped member that fits inside a complementary member or hex socket on the spacer. In essence, different driving tools 66 having different distal bits 76 may be employed depending on the design of the spacer with which it is to be used. The instrument is advantageously configured such that torque placed on the handle 74 of the driving tool 66 while arranging the spacer is countered by grasping the handle assembly 14 to provide a counter-torque preventing twisting or misalignment of the instrument relative to the implantation site.

Figure 13A:
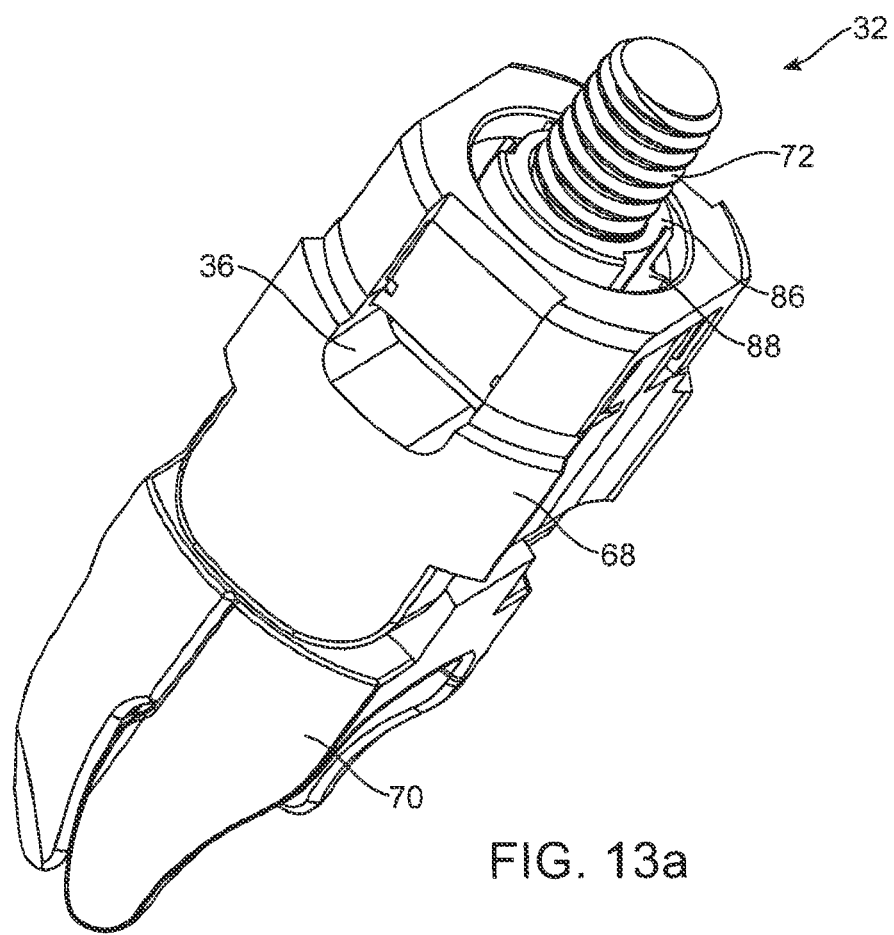
FIG. 13a illustrates a perspective view of a spacer in an undeployed configuration.
Figure 13B:
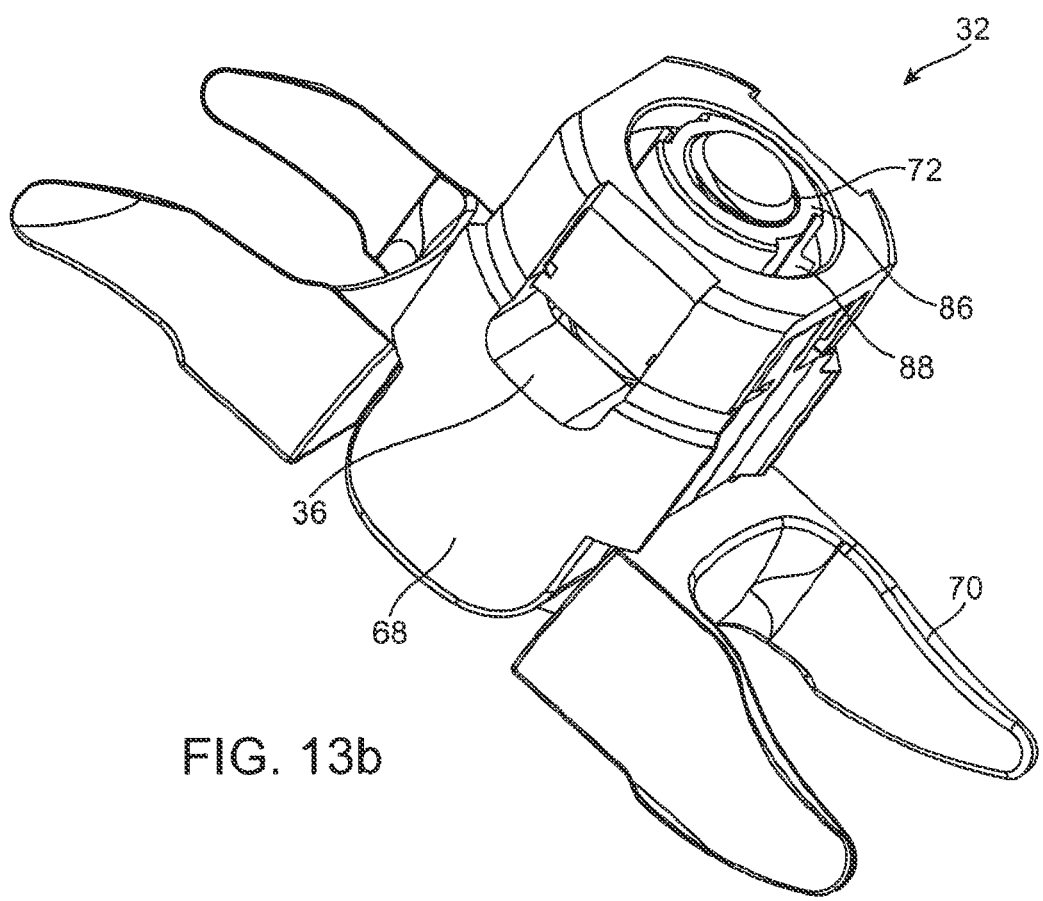
FIG. 13b illustrates a perspective view of a spacer in a deployed configuration.
Figure 14B:
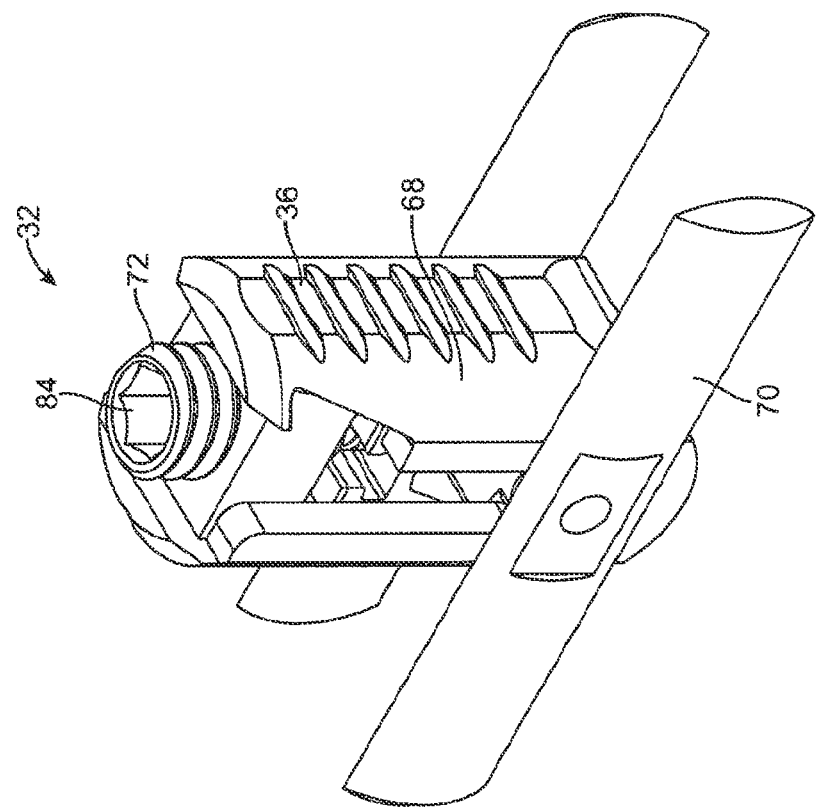
FIG. 14b illustrates a perspective view of a spacer in a deployed configuration.
Figure 14A:
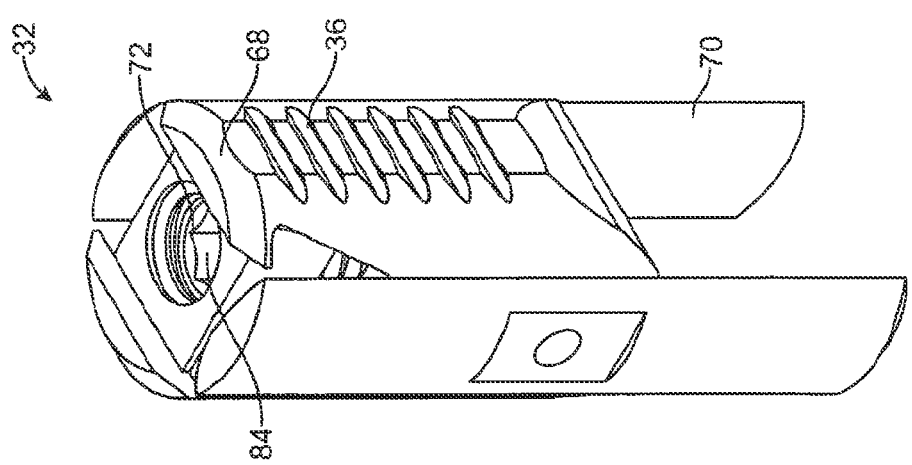
FIG. 14a illustrates a perspective view of a spacer in an undeployed configuration.

The spacer insertion instrument 10 functions to engage with, insert and deploy an interspinous spacer. Illustrative examples of interspinous spacers that are compatible with the insertion instrument are described in applicant's co-pending U.S. patent application Ser. No. 12/217,662 entitled "Interspinous spacer" filed on Jul. 8, 2008 incorporated herein by reference in its entirety, U.S. patent application Ser. No. 12/220,427 entitled "Interspinous spacer" filed on Jul. 24, 2008 incorporated herein by reference in its entirety, U.S. patent application Ser. No. 12/205,511 entitled "Interspinous spacer" filed on Sep. 5, 2008 incorporated herein by reference in its entirety, and U.S. Provisional Patent Application Ser. No. 61/011,199 entitled "Interspinous spacer" filed on Jan. 15, 2008 incorporated herein by reference in its entirety. Examples of such interspinous spacers 32 are shown in FIGS. 12-14 wherein like reference numerals are used to describe like parts. In general, each spacer 32 includes a body portion 68 with at least one prong receiving portion 36 for connecting with the instrument 10, at least one wing 70 rotatably connected to the body portion 68 and an actuator shaft 72 housed in the body portion 68 and configured to arrange the at least one wing 70 from at least one undeployed configuration (see FIGS. 12a, 13a and 14a) to at least one deployed configuration (see FIGS. 12b, 13b and 14b) and vice versa. The at least one wing serves as a body portion 68 stabilizer with respect to at least one adjacent spinous process of a patient's spine and is configured in one variation to cradle an adjacent spinous process on both sides and in another variation forming a seat for an adjacent spinous process.

The spacer insertion instrument 10 utilizes a working channel accessing a patient's spine that is preferably created by the use of one or more tools such as a target needle, K-wire, dilators, mounting bracket, cannula, stabilizing arm, interspinous knife, interspinous reamer, and interspinous gage, all described in applicant's co-pending U.S. patent application Ser. No. 11/582,874 entitled "Minimally invasive tooling for delivery of interspinous spacer" filed on Oct. 18, 2006, incorporated herein by reference in its entirety. The spacer insertion instrument 10 is typically inserted through a cannula having a distal end positioned at the interspinous process space in a minimally invasive, percutaneous, mini-open or open surgical procedure. In some procedures, a cannula is not employed to deliver the instrument 10 and spacer 32 to the interspinous space.

In use, a spacer 32 is placed in juxtaposition to the distal end of the insertion instrument 10 such that the prongs 28 of the instrument 10 are adjacent to the prong receiving portions 36 on the spacer 32. The control 24 is then activated to clamp the prongs 28 of the inner shaft 20 onto the spacer 32. In particular, the control 24 is rotated in one direction which advances the outer shaft 22 over the inner shaft 20 to thereby inwardly deflect the outwardly extending prongs 28 at the distal end of the inner shaft 20. This inward deflection allows the prongs 28 to engage the spacer body and, in particular, allows the prong extensions 34 to be inserted into the prong receiving portions 36 and with further rotation of the control 24 to lock the instrument 10 securely onto the spacer 32. Reverse rotation of the control 24 translates the outer shaft 22 proximally to expose the prongs 28 allowing them to deflect outwardly to their pre-stressed normal position and thereby release the spacer 32 from the insertion instrument 10.

If a cannula is employed in the operative site, the insertion instrument 10 with the attached spacer 32 in an undeployed configuration is sized to fit through a cannula and is passed through the cannula to the interspinous process space. Once in position inside the patient, a driving tool 66 is inserted into the proximal opening of the central passageway 67 of the instrument and passed until the distal spacer engaging bit 76 of the driving tool 66 connects with the spacer 32. The connection of the driver 66 to the spacer is signaled via tactile feedback of the bit engaging the spacer. Depending on the spacer design, the connection of the driving tool 66 with the spacer 32, in particular the engaging features 80, 82, will be different. In general, however, the driving tool 66 connects to the spacer 32 such that movement, such as rotation and/or translation, of the driving tool 66 effects deployment of the at least one wing 70 of the spacer 32. Such deployment of the wings is continuous with the rotation and/or translation of the driving tool. As a result, the deployment may be stopped by stopping such rotation making the deployment incremental. Such incremental deployment allows the surgeon to observe incremental deployment progress via fluoroscopic observation inbetween rotations to help properly position the instrument. Hence, the spacer and instrument combination provides incremental and continous deployment unlike other spacer/installment combinations that only have one deployed configuration and one undeployed configuration with no intermediate configurations or means provided by the instrument to gradually arrange the spacer therebetween. In particular and with respect to the spacer embodiments shown in FIGS. 12-14, movement, such as rotation and/or translation, of the driving tool effects translation of the actuator shaft 72 which in turn is connected to the at least one wing 70 causing it to deploy into an expanded configuration.

With particular reference now to FIGS. 12a and 12b, the driving tool 66 that is configured to connect with the spacer shown in FIGS. 12a and 12b will have a spacer engaging bit 76 that has a hexagonally shaped member that is sized to fit inside the complementarily hexagonally shaped interior 84 of the actuator shaft 72. With the instrument 10 operatively positioned inside the patient and with the driving tool engaged to the actuator shaft 72, rotation of the driving tool 66 distally advances the actuator shaft 72 to deploy the wings 70 into the configuration shown in FIG. 12b. Of course, any polygonal or other shape may be employed. Reverse rotation of the driving tool 66 will proximally retract the actuator shaft 72 to undeploy the wings 70.

Figure 18:
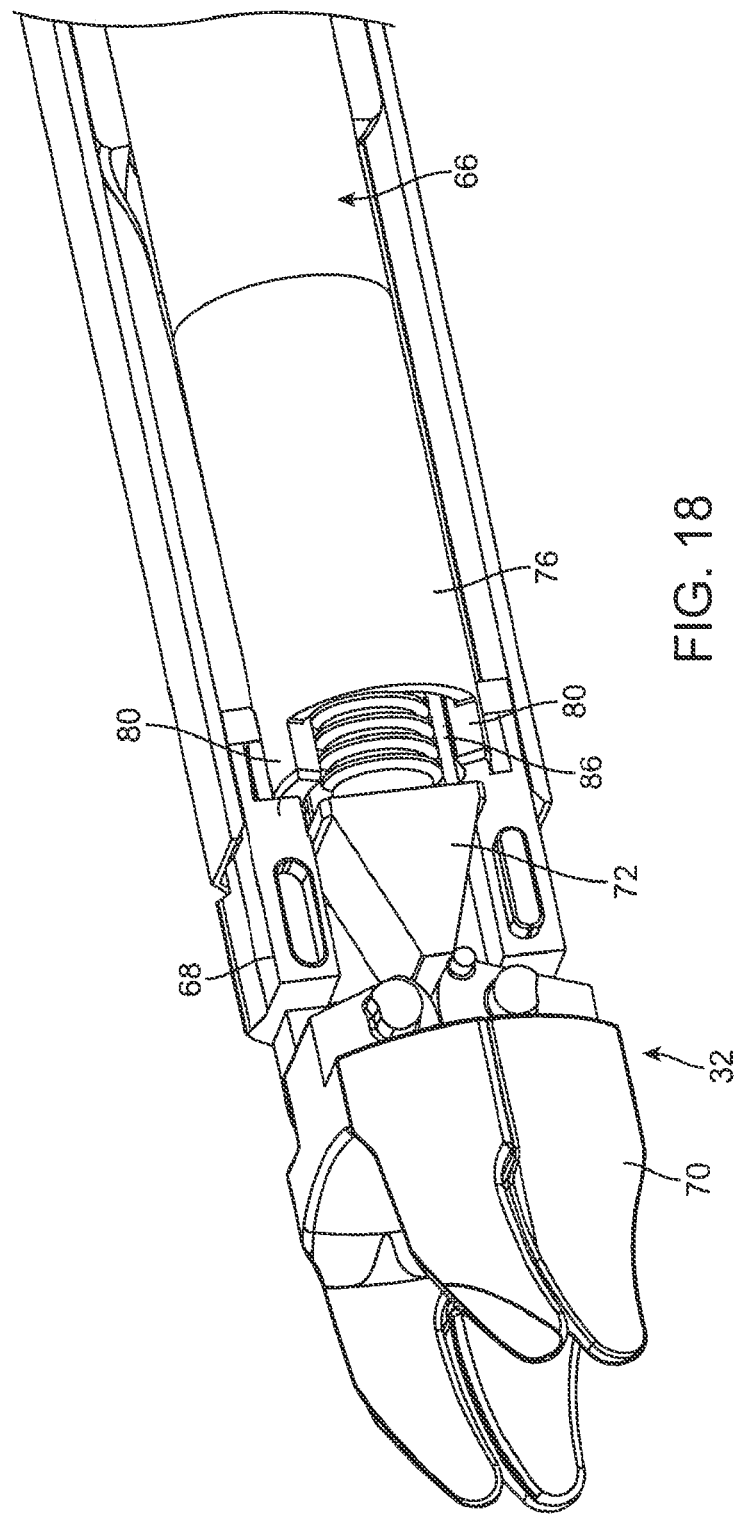
FIG. 18 illustrates a partial cross-sectional view of a spacer insertion instrument and driving tool connected to a spacer in an undeployed configuration according to the present invention.
Figure 19:
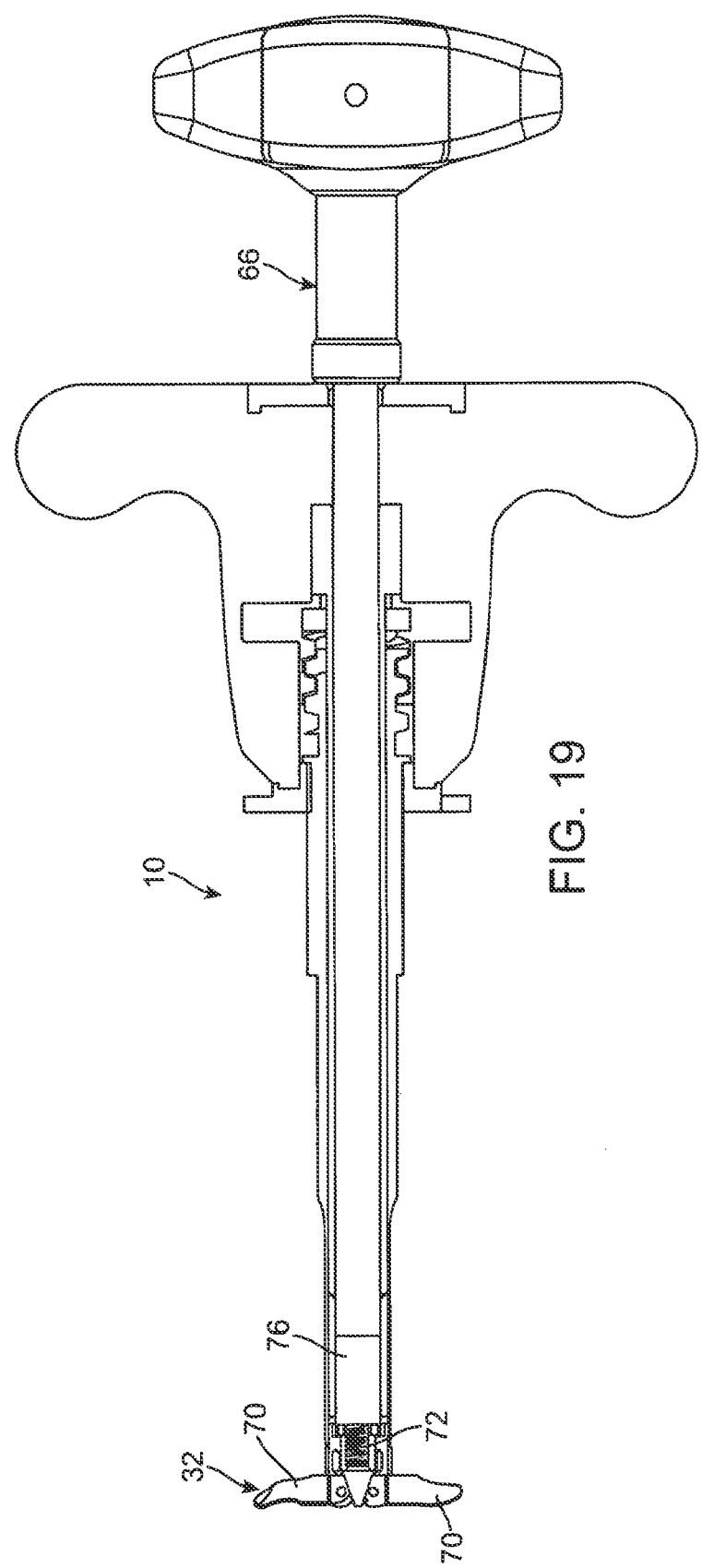
FIG. 19 illustrates a cross-sectional view of a spacer insertion instrument and driving tool connected to a spacer in a deployed configuration according to the present invention.

With particular reference now to FIGS. 13a, 13b and FIGS. 17-20, the driving tool 66 that is configured to connect with the spacer 32 shown in FIGS. 13a and 13b will have a configuration of the like shown in FIGS. 15a, 15b and 15c wherein the spacer engaging bit 76 includes two projecting features 80. The two projecting features 80 engage complementary features 88 on a spindle 86 located inside the body portion 68 of the spacer 32 as shown in FIG. 18. Once engaged to the spindle 86 (see FIG. 17), rotation of the driving tool 66 rotates the spindle 86 which in turn advances the actuator shaft 72 to deploy the wings 70 into the configuration shown in FIGS. 13b, 19 and 20. As can be seen in these figures, when in the deployed configuration, the actuator shaft 72 is distally translated with rotation of the driving tool. Reverse rotation of the driving tool 66 will turn the spindle 86 in an opposite direction and proximally translate the actuator shaft 72 to undeploy the wings 70 into position shown in FIGS. 13a and 17.

With particular reference now to FIGS. 14a and 14b, the driving tool 66 that is configured to connect with the spacer shown in FIGS. 14a and 14b will have a spacer engaging bit 76 that has a hexagonally shaped member that is sized to fit inside the complementarily hexagonally shaped interior 84 of the actuator shaft 72. With the instrument 10 operatively positioned inside the patient and with the driving tool engaged to the actuator shaft 72, rotation of the driving tool 66 proximally advances the actuator shaft 72 to deploy the wings 70 into the configuration shown in FIG. 14b. Of course, any polygonal or other shape may be employed and reverse rotation of the driving tool 66 will distally advance the actuator shaft 72 to undeploy the wings 70.

For all of the spacer embodiments described above with which the insertion instrument 10 may be used, the driving tool 66 is activated by rotation. However, the driving tool may be activated by translation to deploy a spacer of the like described in applicant's co-pending U.S. patent application Ser. No. 11/314,712 entitled "Systems and methods for posterior dynamic stabilization of the spine" filed on Dec. 20, 2005 and U.S. patent application Ser. No. 11/593,995 entitled "Systems and methods for posterior dynamic stabilization of the spine" filed on Nov. 7, 2006, both of which are incorporated herein by reference in their entireties. Other examples of spacers with which the insertion instrument or modified version thereof may be employed are disclosed in U.S. patent application Ser. No. 11/079,006 entitled "Systems and methods for posterior dynamic stabilization of the spine" filed on Mar. 10, 2005 and U.S. patent application Ser. No. 11/190,496 entitled "Systems and methods for posterior dynamic stabilization of the spine" filed on Jul. 26, 2005 both of which are incorporated herein by reference in their entireties.

Furthermore, the driving tool may be activated by rotation and translation of the driving tool to deploy the spacers of the like shown in FIGS. 12a, 12b, 14a and 14b. Activation of the driving tool to deploy the spacer that involves translation of the driving tool advantageously provides the user with a degree of deployment information. This feature is particularly important because positioning and deployment of the instrument and spacer may result in the wings 70 abutting tissue, bone or other obstructions within the patient that would signal to the user to either reposition the instrument and spacer or clear any obstructions. An example of a degree of deployment information feature includes translation of the driving tool. For example, if translation of the driving tool is less than a specific marker or distance, the user will know that the spacer is not fully deployed or that there is some obstruction and further movement of the driving tool, repositioning or removal of an obstruction is required for full deployment. In one variation, the handle 74 of the driving tool 66 rests a certain distance from the proximal end of the handle assembly 14 and with rotation, the driving tool 66 advances until the handle 74 of the driving tool contacts the proximal end of the handle assembly 14. In another variation, the middle shaft 78 of the driving tool 66 includes markings that indicate to the user the distance that the driving tool has moved distally or proximally to provide a degree of deployment information.

Of course, the spacer may have more than one deployed configuration as well as more than one undeployed configuration as the system permits varying degrees of deployment according to surgeon preference. Also, the deployment is reversible such that along any stage of deployment the driving tool can change the direction of translation of the actuator shaft of the spacer and hence, reverse deployment of the wings. The degree of translation of the actuator shaft and hence deployment of the spacer is variable. This variability advantageously permits the spacer to have multiple deployment configurations. Also, at intermediate levels of deployment, the spacer in conjunction with the instrument serves as a customized distractor. Once the spacer is in position and in the desired deployed configuration between adjacent interspinous processes of a patient's spine, the control 24 is activated in an opposite direction to release the prongs 28 and disconnect the spacer from the instrument. The insertion instrument is then removed from the patient leaving the spacer in place. With the spacer in place, the wings cradle the spinous processes. If two wings are employed, they cradle both of the adjacent spinous processes for a given interspinous process space. The spacer body alone, the wings alone, or the body in conjunction with one or more of the wings space apart the adjacent spinous processes and as a result, the implanted spacer opens the spinal canal, maintains the desired distance between vertebral body segments, and as a result, avoids impingement of nerves and relieves pain.

The insertion instrument can also be used to remove a spacer from the patient or to adjust its position following deployment. In such a case, the insertion instrument is inserted into a cannula, if one is employed, the cannula being accessed to an interspinous process space of a patient and positioned proximate to the spacer located in the interspinous space. Then the control 24 is activated to connect the instrument to the body with tactile feedback of the connection provided by the instrument configuration. A driving tool 66 is also inserted and connected to the spacer to undeploy the spacer wings. With the wings in at least one undeployed configuration, the spacer can then be removed or repositioned and redeployed.

In typical applications, the insertion instrument includes a variety of markings, for example, to indicate various status conditions of the tool and the associate interspinous spacer. In an alterative arrangement, the markings are selected as conventional visible markings or may be radio-opaque. The insertion instrument may also be optionally arranged with one or more markers selected, for example, from ultrasonic, magnetic markers or other marker types to advantageously avoid the need for fluoroscopy.

The disclosed devices or any of their components can be made of any biologically adaptable or compatible materials including PEEK, PEK, PAEK, PEKEKK or other polyetherketones. Materials considered acceptable for biological implantation are well known and include, but are not limited to, stainless steel, titanium, tantalum, combination metallic alloys, various plastics, polymers, resins, ceramics, biologically absorbable materials and the like. In one variation, the instrument includes a substantially radiolucent portion connected to a substantially non-radiolucent portion. For example, the non-radiolucent portion may be comprised of at least a portion of the first assembly 12 and the radiolucent portion may be comprised of at least a portion of the handle assembly 14. The substantially non-radiolucent portion is a substantial portion of radiolucent material that is exclusive of small fasteners or other features found scattered in a radiographic projection. The substantially non-radiolucent portion has a radiographic projection on a plane perpendicular to the longitudinal axis that is substantially coincident with a radiographic projection of a connected spacer on said plane when in at least one undeployed configuration. This feature is advantageous for minimilly invasive surgical procedures wherein fluoroscopic observations assist the surgeon in correct placement of an implant while providing the patient with less tissue intrusion that would otherwise be the case in larger incisions or open surgical procedures because the substantial radiolucent portions of the instrument do not obstruct fluoroscopic imaging of the implantation site for positioning and guiding the implant. This is the case when the instrument is connected to a spacer, inserted posteriorly with radiographic projections taken along a substantially anterior-posterior view of the patient's body. This is also the case when the instrument is used to deploy the spacer into at least one deployed configuration wherein the radiographic or non-radiographic projection of the spacer on a plane perpendicular to the longitudinal axis is substantially coincident with a radiographic projection of a substantial portion of the instrument made of substantially non-radiolucent material. However, the instrument and spacer are configured such that when the wings are arranged in at least one deployed configuration, the projection of the deployed wings on said plane extend beyond the perimeter of the projection of non-radiolucent portions such that the wings and their position can be observed under fluoroscopic observation, thereby, the physician can see the deployment of the wings without obstruction from the rest of the instrument and then undeploy and redeploy the wings as necessary or reposition the instrument for proper placement of the spacer and improve implantation according to patient anatomy. Therefore, this instrument and spacer system greatly improves ease of implantation for the surgeon, reduces surgery time, increases patient recovery and significantly improves upon minimally invasive techniques. In one variation, the non-radiolucent portion substantially comprises a spacer connecting shaft. In one variation, non-radiolucent portions include the shaft 78 of the driving tool 66 and radiolucent portion include the handle 74 of the driver 66.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. A method for implanting an interspinous device having a spacer body and first and second wings, the method comprising:
    inserting the interspinous device between a first spinous process and a second spinous process of a subject's spine while an instrument is connected to the interspinous device;
    deploying the interspinous device by rotating a driving tool of the instrument to rotate the first and second wings relative to the spacer body such that the first and second wings are positioned to hold the first and second spinous processes; and
    disconnecting the interspinous device from the instrument by rotating a control of the instrument while the first and second wings are positioned to hold the first and second spinous processes and the control is located outside of the subject.

2. The method of claim 1 wherein deploying the interspinous device includes rotating the driving tool while a prong of the instrument is positioned within a prong receiving portion of the interspinous device such that the prong limits rotation of the spacer body.

3. The method of claim 1 wherein disconnecting the interspinous device from the instrument includes moving prongs of the instrument from a clamping configuration for holding the interspinous device to an open configuration for releasing the interspinous device.

4. The method of claim 1 wherein the instrument includes a clamping assembly and a handle, and wherein rotating the driving tool includes
    rotating the driving tool about an axis of rotation defined by the clamping assembly while the driving tool extends through the clamping assembly and extends through the handle positioned outside of the subject.

5. The method of claim 1 wherein the driving tool includes a proximal end with a driver handle and a distal end with an engaging bit, and wherein deploying the interspinous device includes
    manually rotating the driver handle positioned proximally of a clamping tool of the instrument while the clamping tool of the instrument holds the spacer body and the engaging bit engages an actuation mechanism of the interspinous device, wherein the actuation mechanism is configured to rotate the first and second wings as the control rotates.

6. The method of claim 1 wherein disconnecting the interspinous device from the instrument includes moving a clamping assembly of the instrument from a clamping configuration for holding the interspinous device to a release configuration for releasing the interspinous device.

7. The method of claim 1 wherein
    the instrument includes
        a handle, and
        a clamping assembly coupleable to the handle, wherein the clamping assembly includes at least one prong, an outer shaft, and an inner shaft with a passageway for receiving the driving tool; and
    disconnecting the interspinous device from the instrument includes moving the at least one prong out of a prong receiving portion of the interspinous device by moving one of the outer and inner shafts.

8. The method of claim 7 wherein disconnecting the interspinous device includes rotating the control to move one of the outer and inner shafts with respect to the other to cause the at least one prong to move toward and/or away from a longitudinal axis of the instrument.

9. The method of claim 1 wherein disconnecting the interspinous device from the instrument includes opening a clamping assembly of the instrument configured to hold the interspinous device.

10. The method of claim 1 wherein the instrument has a distal end that clamps onto the interspinous device, wherein rotation of the control causes the distal end to open and release the interspinous device.

11. A method for implanting an interspinous device having a spacer body and first and second wings using an instrument, the method comprising:
    positioning the interspinous device at an interspinous space between a first spinous process and a second spinous process of a subject's spine while the interspinous device is connected to the instrument, wherein the instrument includes a handle, an assembly, a driving tool, and a control;
    moving the driving tool relative to the spacer body releasably held by the assembly to cause an actuator mechanism of the interspinous device to drive the first and second wings toward a deployed configuration for holding the first and second spinous process;

after deploying the first and second wings, rotating the control positioned external to the subject to cause the assembly to release the interspinous device; and after releasing the interspinous device, removing the instrument from the subject while the first spinous process is between elongate arms of the first wing and the second spinous process is between elongate arms of the second wing.

12. The method of claim 11 wherein the driving tool is configured to be rotated independent of rotation of the control to rotate the first and second wings independently of the release of the interspinous device.

13. The method of claim 11 wherein rotating the control of the instrument includes rotating the control a sufficient amount to move prongs of the instrument out of respective prong receiving portions of the interspinous device and thereby release the interspinous device.

14. The method of claim 11 wherein
the instrument includes a clamping assembly movable from clamping configuration for holding the interspinous device to an open configuration for releasing the interspinous device, and rotating the control of the instrument includes rotating the control a sufficient amount to move the clamping assembly toward the open configuration so as to release the interspinous device.

15. The method of claim 11 wherein moving the driving tool includes rotating the driving tool about an axis of rotation defined by a clamping assembly of the instrument while the driving tool is positioned within a passageway of the clamping assembly.

16. The method of claim 11 wherein
the driving tool includes a proximal end with a driver handle and a distal end with an engaging bit, and moving the driving tool includes manually rotating the driver handle positioned proximally of a clamping assembly of the instrument while the engaging bit engages the interspinous device held by the clamping assembly.

17. The method of claim 11 wherein rotating the control of the instrument causes a clamping assembly of the instrument to move from an clamping configuration for holding the interspinous device to a release configuration for disconnecting from the interspinous device.

18. The method of claim 11 wherein
the instrument includes a handle and a clamping assembly coupleable to the handle, wherein the clamping assembly includes an outer shaft and an inner shaft with a passageway for receiving the driving tool, and rotating the control includes moving the control a sufficient amount to move at least one prong out of a prong receiving portion of the interspinous device.

19. The method of claim 18 wherein rotation of the control causes one of the outer and inner shafts to move with respect to the other to cause the at least one prong to move toward or away from a longitudinal axis of the instrument.

20. The method of claim 11 wherein the instrument includes an assembly having a distal end with a clamping assembly, wherein rotation of the control includes moving the clamping assembly between a clamping configuration for holding the interspinous device and an open configuration for releasing the interspinous device independent of rotation of the driving tool.

21. The method of claim 11, further comprising moving the interspinous device along a midline approach to position the interspinous device at the interspinous space.

* * * * *